US012734354B2

(12) United States Patent
Shepherd et al.

(10) Patent No.: US 12,734,354 B2
(45) Date of Patent: Sep. 15, 2026

(54) PERIPHERAL NERVE ELECTRODE ARRAY

(71) Applicant: THE BIONICS INSTITUTE OF AUSTRALIA, East Melbourne (AU)

(72) Inventors: Robert K. Shepherd, East Melbourne (AU); James Fallon, East Melbourne (AU); Sophie Payne, East Melbourne (AU); Owen Burns, East Melbourne (AU); John Barton Furness, East Melbourne (AU)

(73) Assignee: THE BIONICS INSTITUTE OF AUSTRALIA, East Melbourne (AU)

( * ) Notice: Subject to any disclaimer, the term of this patent is extended or adjusted under 35 U.S.C. 154(b) by 0 days.

(21) Appl. No.: 17/518,112

(22) Filed: Nov. 3, 2021

(65) Prior Publication Data

US 2022/0054825 A1 Feb. 24, 2022

Related U.S. Application Data

(63) Continuation of application No. 16/844,286, filed on Apr. 9, 2020, which is a continuation of application No. PCT/AU2018/051240, filed on Nov. 20, 2018.

(51) Int. Cl.

*A61N 1/36* (2006.01)
*A61B 5/388* (2021.01)
*A61N 1/05* (2006.01)

(52) U.S. Cl.

CPC ............ *A61N 1/0558* (2013.01); *A61B 5/388* (2021.01); *A61N 1/36007* (2013.01); *A61N 1/36053* (2013.01)

(58) Field of Classification Search

CPC ...... A61B 5/24; A61B 5/4041; A61N 1/0556; A61N 1/0558; A61N 1/36007;

(Continued)

(56) References Cited

U.S. PATENT DOCUMENTS 5,038,781 A 8/1991 Lynch
5,938,596 A 8/1999 Woloszko et al.

(Continued)

FOREIGN PATENT DOCUMENTS

WO WO-2015/066617 A1 5/2015
WO WO-2016/022867 A2 2/2016

OTHER PUBLICATIONS

Bracken, Michael B. "Why animal studies are often poor predictors of human reactions to exposure." Journal of the Royal Society of Medicine 102.3 (2009): 120-122.*

(Continued)

*Primary Examiner* — Allen Porter

(74) *Attorney, Agent, or Firm* — MARSHALL, GERSTEIN & BORUN LLP

(57) ABSTRACT

The present disclosure relates to a peripheral nerve electrode array that includes a first, second and third pair of electrodes spaced from each other along a longitudinal axis of the electrode array, the second pair of electrodes being located between the first and third pairs of electrodes. The present disclosure further relates to method for treating or preventing a chronic inflammatory condition in a human subject in need thereof, comprising providing to the human subject a therapeutically effective electrical stimulation of the anterior central abdominal vagus nerve or the posterior central abdominal vagus nerve, wherein the electrical stimulation is provided through two or more previously implanted electrodes at a site below the cardiac branches and above the hepatic-celiac branches of the nerve; and whereby the chronic inflammatory condition is prevented or treated in the human subject. In addition, the present disclosure relates to a method for treating or preventing a chronic inflammatory condition in a human subject in need thereof.

6 Claims, 17 Drawing Sheets

(58) Field of Classification Search
CPC .............. A61N 1/36053; A61N 1/3606; A61N 1/36146; A61N 1/37247; A61N 1/0507; A61N 1/0509; A61N 1/36; A61N 1/36057
See application file for complete search history.

(56) References Cited

U.S. PATENT DOCUMENTS

| | | | | |
|---|---|---|---|---|
| 8,478,428 | B2 | 7/2013 | Cowley | |
| 8,504,161 | B1 * | 8/2013 | Kornet | A61N 1/36053 607/2 |
| 8,855,775 | B2 | 10/2014 | Leyde | |
| 2004/0249416 | A1 * | 12/2004 | Yun | A61N 1/36189 607/2 |
| 2009/0118780 | A1 * | 5/2009 | DiLorenzo | A61N 1/36007 607/2 |
| 2009/0143831 | A1 * | 6/2009 | Huston | A61N 1/36053 607/2 |
| 2010/0121405 | A1 | 5/2010 | Ternes et al. | |
| 2011/0015695 | A1 * | 1/2011 | Pasricha | A61N 1/05 607/40 |
| 2012/0303080 | A1 * | 11/2012 | Ben-David | A61N 1/36114 607/119 |
| 2013/0261721 | A1 | 10/2013 | Ben-David et al. | |
| 2014/0031910 | A1 | 1/2014 | Fisher et al. | |
| 2014/0046407 | A1 * | 2/2014 | Ben-Ezra | A61N 1/36053 607/72 |
| 2014/0142653 | A1 | 5/2014 | Osorio | |
| 2015/0366467 | A1 | 12/2015 | De Kock et al. | |
| 2016/0331326 | A1 | 11/2016 | Xiang et al. | |
| 2017/0296811 | A1 | 10/2017 | Sharma | |

OTHER PUBLICATIONS

Browning, Kirsteen N et al. "The Vagus Nerve in Appetite Regulation, Mood, and Intestinal Inflammation." Gastroenterology vol. 152,4 (2017): 730-744. doi:10.1053/j.gastro.2016.10.046.*

Koopman, Frieda A et al. "Vagus nerve stimulation inhibits cytokine production and attenuates disease severity in rheumatoid arthritis." Proceedings of the National Academy of Sciences of the United States of America vol. 113,29 (2016): 8284-9. doi: 10.1073/pnas.1605635113.*

International Search Report issued in PCT Patent Application No. PCT/AU2018/051240 dated Jan. 30, 2019.

Written Opinion issued in PCT Patent Application No. PCT/AU2018/051240 dated Jan. 30, 2019.

Supplementary European Search Report issued in European Patent Application No. 18/878,074 dated Jun. 8, 2021.

Levine et al., "Neurostimulation of the Cholinergic Anti-Inflammatory Pathway Ameliorates Disease in Rat Collagen-Induced Arthritis", PLOS ONE, vol. 9, Issue 8, e104530, pp. 1-8, Aug. 2014.

Payne et al., "Abdominal vagus nerve stimulation alleviates collagen-induced arthritis in rats", Frontiers in Neuroscience, pp. 1-12, DOI: 10.3389, Nov. 21, 2022.

Stakenborg et al., "Electrical Stimulation of the Abdominal Vagus Nerve is as Effective as Cervical Nerve Stimulation in Reducing Postoperative Ileus," AGA Abstracts, Su1563-1565, Apr. 2017.

Olofsson et al., "Single-Pulse and Unidirectional Electrical Activation of the Cervical Vagus Nerve Reduces Tumor Necrosis Factor in Endotoxemia" Bioelectronic Medicine 2:37-42, 2015.

Schopf et al., "Rat models of arthritis: Similarities, differences, advantages, and disadvantages in the identification of novel therapeutics", edited by Stevenson et al., In Vivo Models of Inflammation, vol. 1, 2nd Edition, pp. 1-38 (2006).

Tesser et al., "Vagus nerve-mediated neuroimmune modulation for rheumatoid arthritis: a pivotal randomized controlled trial", Nature Medicine, pp. 1-18, DOI: 10.1038 (2025).

Zannad, et al., "Chronic vagal stimulation for the treatment of low ejection fraction heart failure: results of the NEural Cardiac TherApy foR Heart Failure (NECTAR-HF) randomized controlled trial", European Heart Journal, 36:425-433 (2015).

* cited by examiner

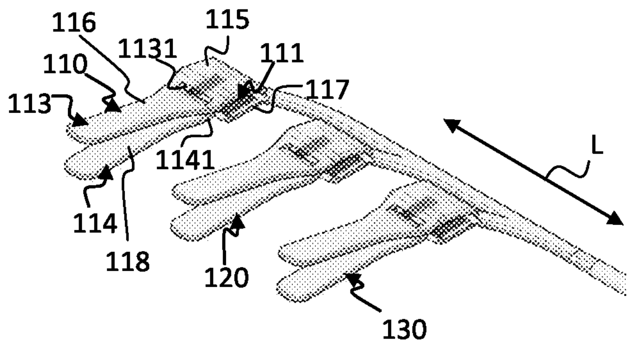
Fig. 3
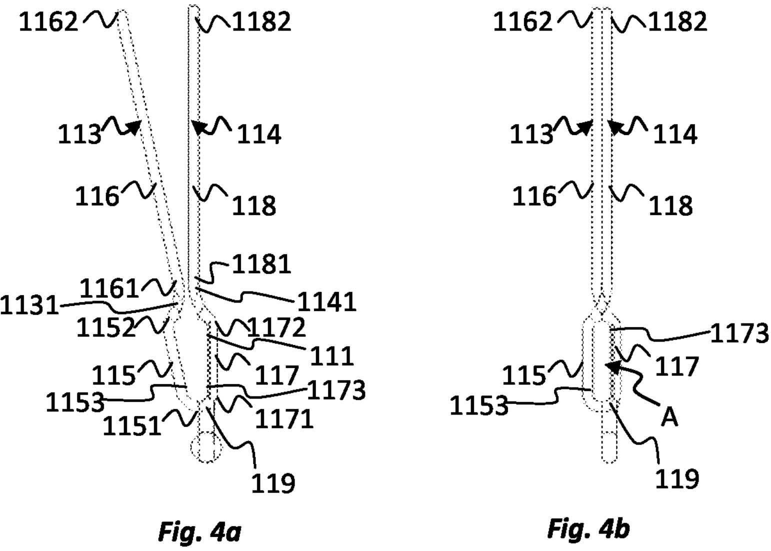
Fig. 4a
Fig. 4b

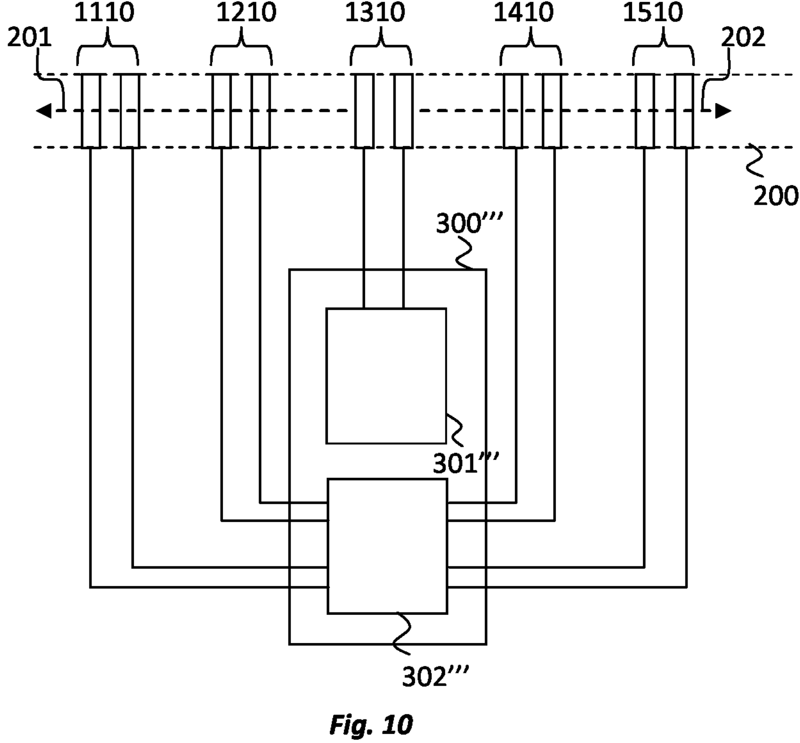
Fig. 10
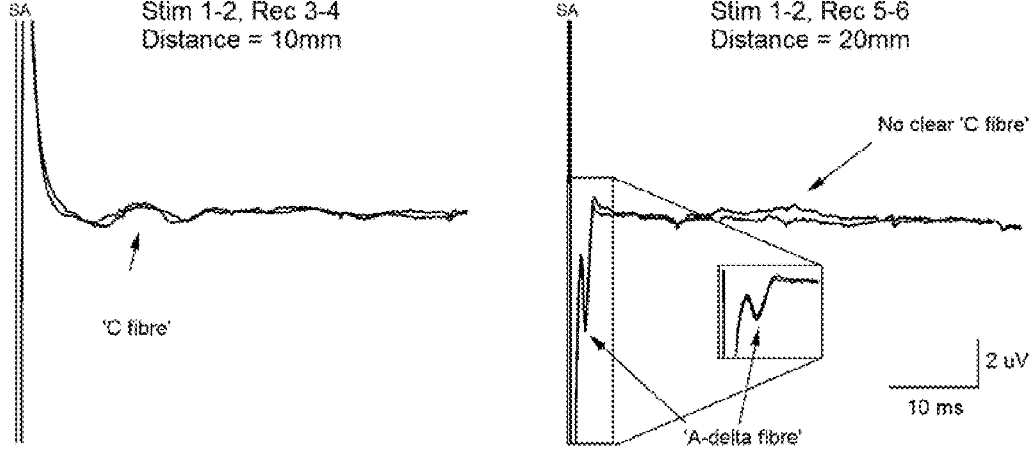
Fig. 11a
Fig. 11b

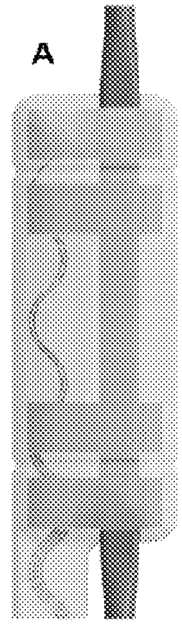
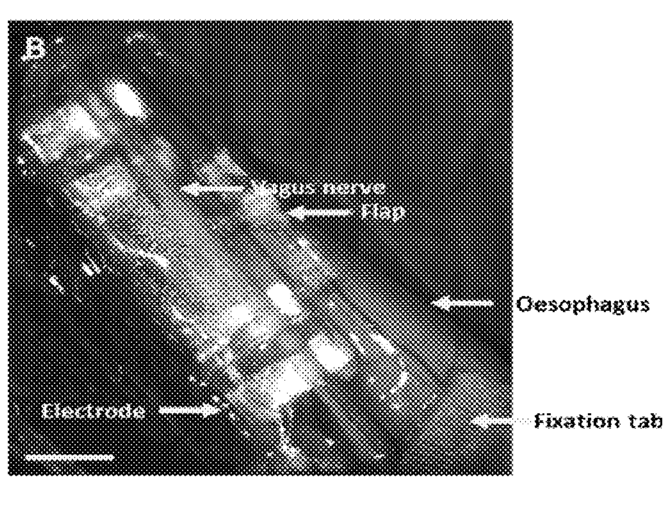
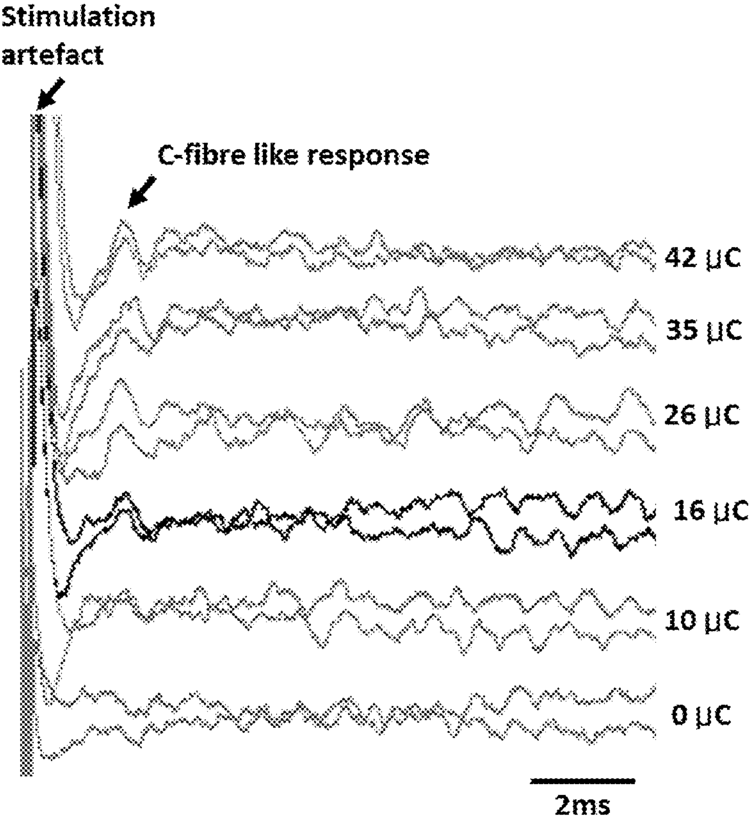
*Fig. 16*

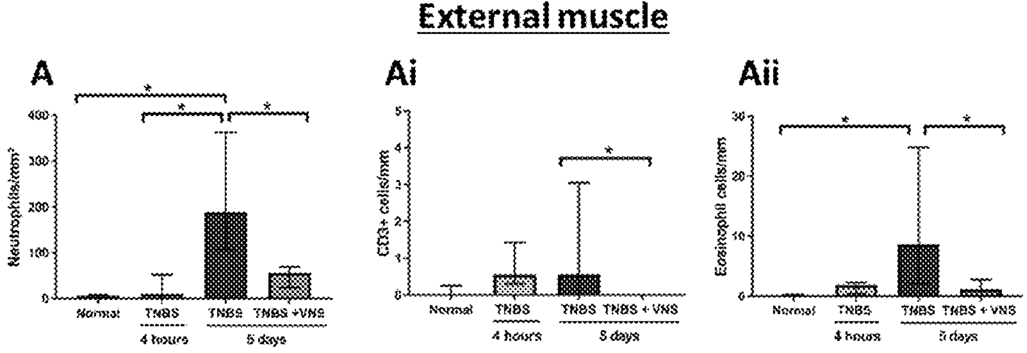
*Fig. 19*
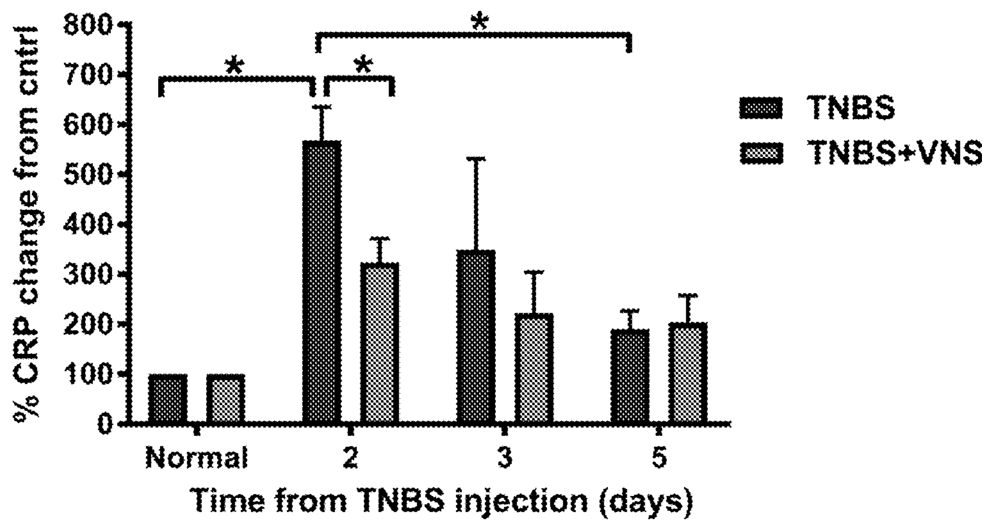

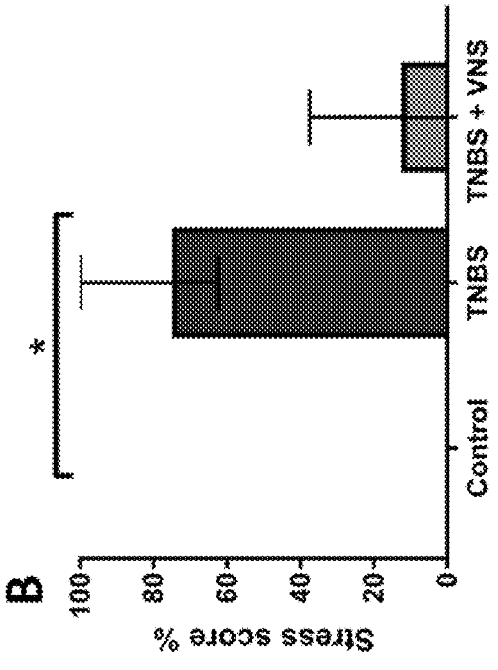
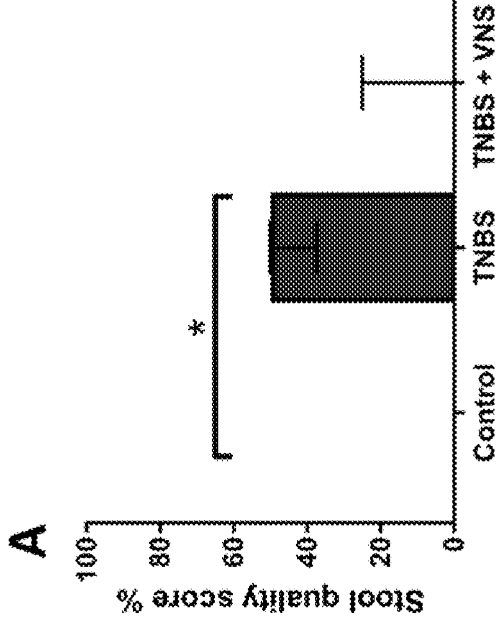
*Fig. 21*

PERIPHERAL NERVE ELECTRODE ARRAY

CROSS-REFERENCE TO RELATED APPLICATIONS

The present application is a continuation application of, and claims benefit of priority to U.S. patent application Ser. No. 16/844,286, filed Apr. 9, 2020, and entitled "Peripheral Nerve Electrode Array," which in turn is a continuation application of PCT/AU2018/051240, filed Nov. 20, 2018 and entitled "Peripheral Nerve Electrode Array," which, in turn, claims priority under 35 U.S.C. § 119 to Australian provisional patent application nos. 2017904684 and 2017904685, filed 20 Nov. 2017, and to Australian provisional patent application no. 2018904157, filed Nov. 1, 2018, the contents of each of which applications being incorporated herein by reference in its entirety and for all purposes.

TECHNICAL FIELD

The present disclosure relates to stimulation, modulation and/or monitoring using electrodes implanted in a subject and specifically through the application of electrical signals to and/or the receiving of electrical signals from the peripheral nervous system. The present disclosure further relates to methods and systems for treating or preventing chronic inflammatory conditions, particularly Inflammatory Bowel Disease.

BACKGROUND

Neurostimulation is the purposeful modulation of activity in a subject's nervous system. Neurostimulation can be carried out invasively, by applying electrical stimulation to the nervous system using implanted electrodes, for example, or non-invasively, using transcranial magnetic or electrical stimulation, for example.

Implanted electrodes can be brought into contact with a peripheral nerve in order to apply the electrical stimulation. The electrical response of the nerve to the neurostimulation can be monitored from additional electrodes in contact with the nerve.

Recently, electrical stimulation of the vagus nerve has been proposed as an alternative approach to treatment of IBD. However, to date this method is associated with a number of off-target side effects including changes in heart rate, changes in breathing, voice alterations, and coughing due to neuromodulation of the heart, lungs, and larynx by the vagus nerve. Thus, there is an ongoing need for new treatments for IBD that are therapeutically effective, cost-effective, and minimise potential side effects.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

According to one aspect of the present disclosure there is provided a peripheral nerve electrode array comprising:

a first pair of electrodes, the first pair of electrodes comprising two first electrodes located proximate each other along a longitudinal axis of the electrode array;

a second pair of electrodes, the second pair of electrodes comprising two second electrodes located proximate to each other along the longitudinal axis of the electrode array; and a third pair of electrodes, the third pair of electrodes comprising two third electrodes located locate proximate to each other along the longitudinal axis of the electrode array, wherein the second pair of electrodes is located between the first and third pairs of electrodes and wherein the first, second and third pairs of electrodes are spaced from each other along the longitudinal axis of the electrode array.

The first, second and third pairs of electrodes (also referenced herein as first, second and third electrode pairs) may each be selectively operable as a pair of stimulation electrodes, for applying an electrical stimulation signal to the peripheral nerve, and/or as a pair of monitoring electrodes, for monitoring (e.g. recording) an electrical response signal at the peripheral nerve in response to an applied electrical stimulation signal. The electrode array may comprise or may be connected to one or more electrical stimulation devices that generate the electrical stimulation signals to apply, via the respective pair(s) of electrodes, to the peripheral nerve. The electrode array may comprise or may be connected to one or more monitoring devices that receive, from the respective pair(s) of electrodes, the electrical response signals and process the electrical response signals.

In one embodiment the first pair of electrodes is a pair of stimulation electrodes for applying an electrical stimulation signal to the peripheral nerve and the second and third pairs of electrodes are pairs of monitoring electrodes for monitoring an electrical response signal at the peripheral nerve in response to the electrical stimulation signal applied by the first pair of electrodes.

The provision of at least three pairs of electrodes, which can provide for a pair of stimulation electrodes and two pairs of monitoring electrodes, for example, can have a number of advantages. The present disclosure has recognised that it is desirable to have the ability to place a pair of monitoring electrodes as close as possible, along the longitudinal axis of the peripheral nerve, to the pair of stimulation electrodes, in order to precisely monitor the effects of the electrical stimulation at the peripheral nerve based on the electrical response signal, including for a 'C-fibre' response, for example. However, the closer the pair of monitoring electrodes is to the pair of stimulation electrodes, the greater risk that an electrical stimulation artefact will dominate the electrical response signal, including any 'A-delta fibre' response. Accordingly, if only one pair of monitoring electrodes is provided in a fixed relationship relative to the pair of stimulating electrodes, the two pairs of electrodes may need to be located relatively far apart to reduce the risk that no suitable electrical response signals will be monitored and/or to allow certain fibre responses to be picked up. By providing a further pair of monitoring electrodes (the third pair of electrodes), spaced further along the longitudinal axis of the peripheral nerve from the pair of stimulating electrodes (the first pair of electrodes) than the other pair of monitoring electrodes (the second pair of electrodes), this problem can be negated. In particular, one pair of monitoring electrodes (the second pair of electrodes) can be located relatively closely to the first pair of electrodes, at a position that may be at greater risk of recording a stimulation artefact, of a size and duration that would significantly affect the quality of all or part of the recorded response, but that would otherwise provide for precise monitoring of the effects of the electrical stimulation, including for 'C-fibre' response, for example. If there is such a stimulation artefact, the further pair of monitoring electrodes (the third pair of electrodes) can provide a suitable backup or substitute, ensuring that monitoring of the response to electrical stimulation can still be successfully achieved, including for 'A-delta fibre' responses, for example. The electrical neural response signals may be measured as electrically evoked compound action potentials (ECAPs), for example. ECAPs may be measured for specific time periods following electrical stimulation, for example, such as for at least 3 ms, at least 5 ms, at least 7 ms, at least 10 ms, or at last 12 ms, although the particular time period may be varied depending on the distance between stimulating electrodes and recording electrodes. In some embodiments of the present disclosure, the arrangement may allow recording of the electrically evoked compound action potential (ECAP) responses from both slow and fast conducting fibres without obstruction by the stimulation artefact.

In accordance with the above, in one embodiment, the first pair of electrodes is a pair of stimulation electrodes for applying an electrical stimulation signal to the peripheral nerve; the second pair of electrodes is a pair of monitoring electrodes for monitoring a first electrical response signal at the peripheral nerve in response to the electrical stimulation signal applied by the first pair of electrodes; and the third pair of electrodes is another pair of monitoring electrodes for monitoring a second electrical response signal at the peripheral nerve in response to the electrical stimulation signal applied by the first pair of electrodes. The third pair of electrodes can be configured to monitor the second electrical response signal if all or a relevant part of the first electrical response signal is dominated by an electrical stimulation artefact, for example.

Nevertheless, the different pairs of electrodes may be selectively operable in different configurations. For example, the second (middle) pair of electrodes may be selectively operable as a pair of stimulation electrodes for applying electrical stimulation signals to the peripheral nerve and the first and third pairs of electrodes may be selectively operable as pairs of monitoring electrodes for monitoring an electrical response signal at the peripheral nerve. The first and third pairs of electrodes may therefore monitor the electrical response in different directions (e.g. the electrical response in both afferent and efferent directions, rather than the electrical response in an afferent or efferent direction only).

As another example, at least two of the first, second and third pairs of electrodes may be selectively operable as pairs of stimulation electrodes for applying electrical stimulation signals to the peripheral nerve and the remaining one of the first, second and third pairs of electrodes may be selectively operable as a pair of monitoring electrodes for monitoring an electrical response signal at the peripheral nerve. By providing multiple electrical stimulation locations, the direction of electrical activity may be more precisely controlled.

Further, the first, second and third pairs of electrodes may all be selectively operable as pairs of monitoring electrodes for monitoring an electrical response signal at the peripheral nerve. In this and other arrangements described herein, pairs of monitoring electrodes may be used to monitor either evoked neural responses, following application of an electrical stimulation signal and/or spontaneous (e.g. natural/passive) neural activity of the nerve.

Still further, the provision of first, second and third electrode pairs does not preclude the provision of fourth, fifth or yet further electrode pairs, whether for applying electrical stimulation signals and/or monitoring electrical responses. As one example, five electrode pairs may be provided. The central (e.g. third) pair of electrodes may be a selectively operable as a pair of stimulation electrodes for applying electrical stimulation signals to the peripheral nerve and the remaining four (e.g. first, second, fourth and fifth) electrode pairs may be selectively operable as pairs of monitoring electrodes for monitoring an electrical response signal at the peripheral nerve in different directions. The first and second pairs of electrodes may monitor the electrical response in a first direction (e.g. in an afferent direction) and the fourth and fifth pairs of electrodes may monitor the electrical response in a second direction (e.g. in an efferent direction). The approach may provide advantages as set forth above, including to manage stimulation artefacts when monitoring of electrical response signals in two directions.

The first electrodes may be spaced from each other by a distance a1, the second electrodes may be spaced from each other by a distance a2 and the third electrodes may be spaced from each other by a distance a3. The first and second pairs of electrodes may be spaced from each other by a distance b1 and the second and third pairs of electrodes are spaced from each other by a distance b2. The distances between the electrodes within each pair of electrodes may be substantially equal, i.e. it may be that a1=a2=a3, or they may be different. Similarly, the distances between each pair of electrodes may be substantially equal, i.e. it may be that b1=b2, or they may be different. In general, however, the distances b1, b2 between the different pairs of electrodes may be greater than the distances a1, a2, a3 between the electrodes within each pair of electrodes. For example, the ratio between any one or more of distances a1, a2 and a3 and any one or more of distances b1 and b2 may be between 1:1.5 and 1:4, between 1:1.5 and 1:3, or about 1:2.5. In another example, the ratio between any one or more of distances a1, a2 and a3 and any one or more of distances b1 and b2 may be about 1:5.

Additionally, or alternatively, distances between pairs of electrodes may be set based on a type or property of fibres for which recording is desired. Distances b1, b2 between different pairs of electrodes may be determined as a function of a conduction velocity of fibres that can be recorded at particular latencies (or conduction properties). Merely as one example, to record responses with 'C-fibres', a spacing of 5 mm between pairs of electrodes may be used. In this arrangement, at ~1 m/s conduction velocity, 5 mm spacing provides a latency of ~5 ms which may be sufficient to ensure that a response is recorded while minimising stimulus artefact.

The electrodes within each pair of electrodes may be elongated. The direction of elongation of the electrodes may be transverse to the longitudinal axis of the electrode array and therefore to the longitudinal axis of the peripheral nerve. The electrodes within each pair of electrodes may extend parallel to each other. The electrodes within each pair of electrodes may be positioned side by side along the longitudinal axis of the electrode array and along the longitudinal axis of the peripheral nerve.

The first, second and third pairs of electrodes may be in a substantially fixed relationship. The electrode array may comprise a support that substantially maintains the relative orientation and/or location of the pairs of electrodes, that is, with respect to each other. The relative orientation and/or location of the pairs of electrodes may therefore be substantially pre-defined, rather than being selected by a surgeon. The support may comprise resiliently flexible material, which may allow for slight relative movement of the pairs of electrodes, but may nevertheless substantially maintain the relative locations and orientations.

The support may comprise multiple branches at a distal end. For example, the support may comprise, at a distal end, a first branch that supports the first pair of electrodes, a second branch that supports the second pair of electrodes and a third branch that supports the third pair of electrodes. The branches may ensure that contact between the electrode array and the peripheral neve is minimised, the contact being made only at or immediately adjacent each pair of electrodes, rather than contact occurring across the gaps between the pairs of electrodes. The first, second and third branches may converge together towards a proximal end of the electrode array. The support may be provided by a lead, e.g. a stiff lead. The branches may be branched portions of the lead. The branch portions may be rigid or semi-rigid such that a constant spacing and/or relative orientation between the electrode mounting devices is substantially maintained.

Each branch may comprise an electrode mounting device that mounts to the peripheral nerve, bringing a respective pair of electrodes into electrical contact with the peripheral nerve. Through use of the branches or otherwise, the electrode array may, in general, include one or more electrode mounting devices, each electrode mounting device comprising at least one of the pairs of electrodes and being adapted to mount to the peripheral nerve to electrically interface the pair of electrodes with the peripheral nerve. For example, the electrode array may comprise a first electrode mounting device comprising the first electrode pair, a second electrode mounting device comprising the second electrode pair and a third electrode mounting device comprising the third electrode pair, wherein each of the first, second and third electrode mounting devices is adapted to mount to the peripheral nerve to electrically interface the first, second and third pair of electrodes, respectively, with the peripheral nerve.

Each electrode mounting device may be adapted to clamp to the peripheral nerve. Each electrode mounting device may be adapted to form a loop around the peripheral nerve.

Each electrode mounting device may comprise a first wing and a second wing that are adapted to extend on opposite sides of the peripheral nerve and to be engageable with each other to form the loop. The first wing may comprise a first cuff portion and the second wing may comprise a second cuff portion, the first and second cuff portions being engageable with each other to form the loop. Moreover, the first wing may comprise a first elongate extension portion that extends from the first cuff portion and the second wing may comprise a second elongate extension portion that extends from the second cuff portion.

The electrode mounting device as described above may be used in various peripheral nerve electrode arrays to mount to and electrically interface one or more electrodes with the peripheral nerve.

Thus, according to one aspect of the present disclosure, a peripheral nerve electrode array is provided comprising:

- an electrode mounting device comprising one or more electrodes, the electrode mounting device adapted to mount to a peripheral nerve to electrically interface the electrodes with the peripheral nerve;
- the electrode mounting device comprising a first wing and a second wing, the first wing comprising a first cuff portion and a first elongate extension portion extending from the first cuff portion, and the second wing comprising a second cuff portion and a second elongate extension portion extending from the second cuff portion,
- the first and second cuff portions being engageable with each other to form a loop around the peripheral nerve.

In any aspect described herein, the first and second cuff portions may comprise first and second ends, the first ends being connected to each other and the second ends being movable into engagement with each other to form the loop. The electrode mounting device may comprise a pivot such as a hinge or bearing, e.g. a flexible bearing, that connects the first ends of the cuff portions together. The pivot may allow for relative rotation of the first and second cuff portions.

The first and second elongate extension portions may extend from the second ends of the first and second cuff portions, respectively. The length of each elongate extension portion may be greater than the length of each first and second cuff portion. Each elongate extension portion may be an elongate tab. In this regard, each elongate extension portion may be substantially flat strip of material. However, other configurations of the elongate extension portions are possible.

Each cuff portion may have an inner surface with a semi-elliptical, semi-oblong or semi-rectangular profile to contact an outer surface of the peripheral nerve. Related to this, the loop formed by the first and second cuff portions may have an inner surface with an elliptical, oblong or rectangular profile to contact an outer surface of the peripheral nerve.

The electrode array in one or more embodiments of the present disclosure may be shaped to improve an interface characteristic between the nerve and the electrode array. In one form, one or more of the electrode mounting devices of the electrode array are configured to shape the nerve, such as to flatten the nerve and increase a surface area for contacting with corresponding electrode surfaces. The inner surface(s) may thus press against the nerve causing a compression of the nerve until it has completely reshaped. The cuff portions may be arranged to reshape the nerve, while also ensuring that a maximum force and/or maximum pressure applied to the nerve remains under a predetermined limit. For instance, the cuff portions may be shaped and configured (e.g. by material selection) to apply a pressure to the nerve, where the pressure is maintained under a maximum of 30 mm Hg (approx. 4 kPa).

The elongate extension portions may provide assistance to a surgeon in positioning the electrode mounting device relative to the peripheral nerve, and particularly to assist the surgeon with positioning the first and second cuff portions at appropriate positions on opposite sides of the peripheral nerve, prior to engaging the second ends of the first and second cuff portions with each other to form the loop around the peripheral nerve. Due to their length, the first and second elongate extension portions may be relatively easy to feed either side of the peripheral nerve in a direction perpendicular to the longitudinal axis of the peripheral nerve. Moreover, the first and second elongate extension portions may be relatively easy to take hold of once they have been fed either side of the peripheral nerve. By taking hold of and moving the first and second elongate extension portions, a surgeon may move the first and second cuff portions to suitable positions either side of the peripheral nerve and may move the second ends of the first and second cuff portions into engagement to form the loop around the peripheral nerve.

All or part of each of the first and second wings may be flexible. In some embodiments, the flexibility of the first and second wings may decrease towards a distal end. By being more rigid towards their distal ends, the first and second wings may be more easily or reliably fed, distal ends first, either side of the peripheral nerve. Advantageously, such arrangements may enhance usability in surgical manipulation and/or implantation.

The electrode mounting device may include a locking mechanism to secure the first and second wings in the looped configuration. In one embodiment, the locking mechanism is provided in part by an opening in one of the first and second wings, e.g. the first wing. The other wing, e.g. the second wing, may be movable to extend at least partly through the opening. Moving the second wing through the opening may bring the second ends of the first and second cuff portions into engagement to form the loop and may assist in securing the loop configuration. At least the second elongate extension portion of the second wing may be flexible to assist in positioning it towards and extending it through the opening. A distal end of the second extension portion may be extended through the opening.

The second elongate extension portion may have a proximal end connected to the second end of the cuff portion, and an opposite distal end. The width of the second elongate extension portion may taper towards its distal end. The distal end of the second elongate extension portion may be narrower than the opening of the first wing enabling it to be readily inserted through the opening. The proximal end of the second extension portion may be wider than the second end of the second cuff portion and wider than the opening of the first wing. The proximal end of the second extension portion may therefore define a shoulder at a transition between the proximal end of the second elongate extension portion and the second end of the cuff portion. The material forming the shoulder may be deformable in order to extend through the opening. The natural shape of the shoulder may be deformed to fit the shoulder through the opening and may return to its natural shape once through the opening to secure the first and second cuff portions in the looped configuration.

In addition or as an alternative to using the arrangement described above, including the shoulder to secure the first and second cuff portions in the looped configuration, securing of the first and second wings in the looped configuration may be achieved using sutures, staples and/or other locking mechanisms.

In some embodiments, at least part of the first and/or second extension portions of the first and second wings may be removed after the loop is formed. Removal may be achieved by cutting the first and second extension portions, and/or through a manual separation technique. For example, a region of weakness may be formed in the first and/or second elongate extension portions, such as a line of perforations, a tear notch, a score line or otherwise, enabling a user (e.g., surgeon) to remove at least a part of the first and/or second elongate extension portions.

One or more portions of the electrode array may comprise a biocompatible material, such as a medical grade silicone elastomer. For instance, all or part of the support, such as all or part of the lead, branch, wing and/or cuff, may comprise a silicone elastomer. One or more of the electrodes may comprise a biocompatible material, such as platinum.

The electrode array may be used for a variety of purposes such as the treatment and/or monitoring of medical conditions. As non-limiting examples, the electrode array may be used to treat inflammatory bowel disease, to treat faecal/urinary incontinence or constipation, to treat urinary incontinence, to effect locomotion, or otherwise. The electrode array may be used with any peripheral nerve for any purposes, including, as non-limiting examples, the vagus nerve (e.g. to treat inflammatory bowel disease), or the sacral nerve stimulation (e.g. for treatment of faecal/urinary incontinence or constipation), the pudendal nerve stimulation (e.g. for treatment of urinary incontinence), the sciatic nerve (e.g. to effect locomotion) or otherwise. The electrode array may be implanted below branches to vital organs (larynx, heart or lungs). The electrode array may be scaled in size as appropriate for the nerve that is stimulated.

In other aspects provided herein the disclosure relates to stimulation of the vagus nerve for the treatment of or prevention of a chronic inflammatory condition. The vagus nerve is one of twelve cranial nerves, which are nerves that emerge directly from the brain. The right and left cervical vagus nerves emerge from the brain medulla at the jugular foramen, extend via the nodose ganglia into the neck. Each of the left and right vagus nerves branch to form the following (bilaterally): recurrent laryngeal nerve; pharyngeal plexus; pulmonary and cardiac plexuses.

The left and right vagus nerves course along the esophagus to form the esophageal plexus. The vagus nerves then enter the abdomen (below the diaphragm) as the central abdominal vagus nerves, i.e., the anterior and posterior (FIG. 15). The anterior central abdominal vagus (CAV) nerve then divides into the gastric branch (innervating the stomach), the hepatic branch (innervating the liver, pancreas and duodenum), and the celiac branch (innervating the spleen, duodenum, jejunum, ileus and colon up to the left colic flexure). The posterior CAV nerve divides into the gastric vagus nerve (innervating the stomach) and the celiac vagus nerve (innervating the spleen, duodenum, jejunum, ileus and colon (up to the left colic flexure). Vagus nerve stimulation has traditionally been used in the treatment of refractive epilepsy and depression. In order to carry out such treatment, typically, a stimulating device is surgically implanted under the skin of the chest, and a wire is threaded under the skin connecting the device to the left cervical branch of the vagus nerve. The right cervical branch of the vagus nerve is generally not stimulated unless therapy is specifically directed to treatment of heart failure, as this branch of the vagus nerve carries fibres that innervate the pacemaker nodes of the heart. The device sends electrical signals along afferent and efferent fibres of the vagus nerve. Afferent stimulation is relayed through the brainstem, which then sends signals to other areas in the brain, as well as back into the peripheral nervous system. More recently, vagus nerve stimulation, acting through both afferent and efferent pathways has been proposed as a potentially promising approach for the treatment of chronic inflammatory conditions such as Crohn's disease or ulcerative colitis (reviewed in Bonaz et al 2017*, J Intern Med,* 282 (1):46-63). However, to date vagus nerve stimulation regimens for treatment of IBD have been based on those adopted for treatment of other conditions such as epilepsy, which are not particularly well suited for treatment of IBD and entail off-target stimulation associated with a number of side effects including, voice changes, hoarseness, throat pain, cough, headaches, chest pain, breathing problems, and difficulty swallowing. The present inventors have found that stimulating the CAV nerve, particularly at a site below the cardiac branches and above the hepatic-celiac branches, is therapeutically effective for treatment of a chronic inflammatory condition such as IBD, but reduces potential off-target stimulation and side effects associated with stimulation of the vagus nerve at other sites. In addition vagus nerve stimulation at this location makes it possible to stimulate the vagus nerve bilaterally, an approach not feasible for vagus nerve stimulation above the cardiac branch, as such bilateral stimulation would present an unacceptable risk to cardiac function absent a specific intent to modulate cardiac function for a therapeutic endpoint Further the treatment methods described herein may also include CAV nerve stimulation in combination with administration of suitable therapeutic agents, wherein the dosing of such therapeutic agents may be reduced relative to the dosing used for monotherapy.

Accordingly, provided herein is a method for treating or preventing a chronic inflammatory condition in a human subject in need thereof, comprising providing to the human subject a therapeutically effective electrical stimulation of the anterior CAV nerve or the posterior CAV nerve, wherein the electrical stimulation is provided through two or more previously implanted electrodes at a site below the cardiac branches and above the hepatic-celiac branches of the vagus nerve; and whereby the chronic inflammatory condition is treated or prevented in the human subject. In some preferred embodiments the two or more implanted electrodes are located just below the diaphragm of the human subject.

In a related aspect provided herein is a method for treating or preventing a chronic inflammatory condition in a human subject in need thereof, comprising implanting in the human subject two or more electrodes at a site below the cardiac branches and above the hepatic-celiac branches of the vagus nerve, wherein such electrodes are configured to provide a therapeutically effective stimulation of the anterior CAV nerve or the posterior CAV nerve to treat or prevent the chronic inflammatory condition.

In some embodiments the chronic inflammatory condition to be treated or prevented is inflammatory bowel disease (IBD). In some embodiments the type of IBD to be treated is Crohn's disease or ulcerative colitis. In some embodiments, where the type of IBD to be treated is Crohn's disease, the Crohn's disease subtype is selected from the group consisting of Ileocolitis, Ileitis, Gastroduodenal Crohn's Disease, Jejunoileitis, and Crohn's (granulomatous) colitis. In other embodiments, where the type of IBD to be treated is ulcerative colitis, the subtype of ulcerative colitis is selected from the group consisting of ulcerative proctitis, Proctosigmoiditis, left-sided colitis, and Pan-ulcerative colitis.

In other embodiments the chronic inflammatory condition is selected from the group consisting of non-alcoholic steatohepatitis (NASH), asthma, pancreatitis, psoriatic arthritis, ankylosing spondylitis, severe chronic plaque psoriasis, post-operative ileus, and arthritis.

In some embodiments of the method, the anterior CAV nerve is stimulated. In other embodiments, the posterior CAV nerve is stimulated. In further embodiments, both the anterior and posterior CAV nerve are stimulated. In some embodiments electrical stimulation to the anterior or posterior CAV nerve is provided multiple times. In some embodiments, where bilateral stimulation is to be provided, the stimulation is provided sequentially with stimulation of the anterior and posterior CAV nerves interleaved symmetrically.

In some embodiments, the methods described herein further include detecting one or more evoked responses in the CAV nerve following the stimulation. In some embodiments stimulation settings for the electrical stimulation are set based on properties of detected evoked responses.

In some embodiments the electrical stimulation to the CAV is generated by an implanted electrical stimulation device. In other embodiments the electrical stimulation is generated by an electrical stimulation device that is not implanted.

In some embodiments at least two of the two or more implanted electrodes are paired electrodes. In some embodiments the two or more implanted electrodes comprise three implanted electrodes or four implanted electrodes. In some embodiments the two or more implanted electrodes comprise a stimulating electrode and a recording electrode. In further embodiments the two or more implanted electrodes are provided in an implanted electrode array.

In some embodiments of the methods provided herein, the two or more implanted electrodes are monopolar electrodes. In other embodiments the two or more implanted electrodes are multipolar electrodes. In some preferred embodiments the multipolar electrodes are bipolar electrodes. In some embodiments the electrodes are cuff electrodes.

In some embodiments of the provided methods the stimulation comprises delivering biphasic pulses comprising a pulse width from about 100 usec to about 600 usec, an interphase gap of about 25 usec to about 100 usec; a stimulation frequency of about 5 Hertz to about 40 Hertz; a duration of about 10 seconds to 5 minutes, and a current of about 0.2 mA to about 10 mA. In some embodiments, the stimulation comprises delivering biphasic pulses comprising a 200 μsec pulse width, a 50 μsec interphase gap at 10 Hertz for 30 seconds, with a stimulation current of about 1.6 mA.

In some embodiments a method for preventing or treating a chronic inflammatory condition also includes the step of surgically implanting the two or more electrodes at a site below the cardiac branches and above the hepatic-celiac branches of the vagus nerve prior to the electrical stimulation.

In further embodiments a method for preventing or treating a chronic inflammatory condition further includes administering to the subject a therapeutic agent for treating the chronic inflammatory condition. In some embodiments the therapeutic agent is an anti-inflammatory drug, an immunosuppressant, or an antibiotic.

In some embodiments described herein the method is applied as a method for treatment of a chronic inflammatory condition.

In a related aspect provided herein is the use of two or more electrodes for the treatment of an inflammatory bowel disease, wherein the electrodes deliver a therapeutically effective electrical stimulation to the CAV nerve at a site below the cardiac branches and above the hepatic-celiac branches of the vagus nerve.

In a related aspect provided herein is a system for configuring an electrical stimulation device when used according to the methods described herein, the system comprising: two or more implanted electrodes at a site below the cardiac branches and above the hepatic-celiac branches of the vagus nerve, and configured to stimulate a branch of the CAV nerve; a computing device storing or having access to a plurality of electrical stimulation settings and comprising a user interface to enable authorised selection of at least one of the electrical stimulation settings for provision of electrical stimulation by the stimulation device according to the one setting; and the stimulation device communicatively coupled to the computing device to receive and store the selected electrical stimulation setting, the stimulation device being of a size to be readily implantable or carried on the human subject and configured to selectively provide current to the two or more implanted electrodes according to the at least one electrical stimulating setting. In some embodiments such a system also includes an electrode, implanted at the site, which records evoked or spontaneous activity in the stimulated central abdominal nerve.

In another related aspect provided herein is a kit when used according to any of the treatment or prevention methods provided herein, the kit comprising: two or more implantable electrodes adapted to stimulation of a branch of the CAV nerve; a computing device for storing or having access to a plurality of electrical stimulation settings and comprising a user interface to enable authorised selection of at least one of the electrical stimulation settings for provision of electrical stimulation by the stimulation device according to the one setting; and a stimulation device adapted to be communicatively coupled to the computing device to receive and store the selected electrical stimulation setting, the stimulation device being of a size to be readily implantable or carried on the body of the human subject and configured to selectively provide current to the two or more implantable electrodes according to the at least one electrical stimulating setting.

In a further aspect provided herein is the use of two or more electrodes for treating or preventing an inflammatory bowel disease, wherein the two or more electrodes deliver electrical stimulation to the CAV nerve at a site below the cardiac branches and above the hepatic-celiac branches of the vagus nerve.

Throughout this specification the word “comprise”, or variations such as “comprises” or “comprising”, will be understood to imply the inclusion of a stated element, integer or step, or group of elements, integers or steps, but not the exclusion of any other element, integer or step, or group of elements, integers or steps.

BRIEF DESCRIPTION OF DRAWINGS

By way of example only, embodiments of the present disclosure are now described with reference to the accompanying drawings in which:

FIG. 3 shows a close up perspective view of the distal end region of the electrode array of FIG. 1;

FIGS. 4*a* and 4*b* show end views of an electrode mounting device of the electrode array of FIG. 1 in an open and closed configuration, respectively;

FIG. 10 shows a schematic illustration of electrical components of an electrode array according to another alternative embodiment of the present disclosure;

FIGS. 11*a* and 11*b* show electrically evoked compound action potentials (ECAPs) monitored by two monitoring electrode pairs that are spaced at different distances along a peripheral nerve relative to a stimulating electrode pair in an Example 1;

FIG. 16 shows: (A) a rendered drawing of one embodiment of a CAV nerve electrode array including stimulating and recording electrodes. (B) an image of an implanted electrode array on vagus nerve in a rat. (C) an example of recording traces for C-fibre responses to vagus nerve array stimulation (200 μs biphasic pulse width+50 μs interphase gap; 10 Hz). A range of currents was used, as shown by the charge per phase labels on the right hand edge of the figure (μC=μCoulombs).

FIG. 19 shows that vagus nerve stimulation (VNS) reduces leukocyte infiltration into external muscle layers. A-Aii: At 5 days following TNBS injection, the prevalence of neutrophils, and eosinophils increased within circular and longitudinal muscle layers ($P<0.05$). In VNS treated tissue, neutrophils, CD3+ cells and eosinophils were significantly reduced ($P<0.05$). Data show median+interquartile range. Differences between groups ($P<0.05$) were tested using non-parametric Kruskal-Wallis and Dunn's post hoc test.

FIG. 20 shows that systemic inflammation is reduced by VNS following TNBS injection. Peripheral blood was taken for analysis of C-reactive protein (CRP). TNBS injection induced a transient increase in CRP levels at 2 days ($P<0.05$), which significantly decreased to normal levels by day 5 ($P<0.05$). Following VNS treatment, levels of CRP in plasma were significantly lower than in unstimulated animals at 2 days ($P<0.05$). Data ($n=3$/group) were normalised to control values and show mean proportional changes (%)+S.E, and significant differences accepted as $P<0.05$.

FIG. 21 shows bar graphs illustrating the effect of VNS on stool quality and stress levels following injection of TNBS to induce inflammation in rats. (A) Effect of VNS on stool quality; (B) Effect of VNS on stress levels. Stool consistency and signs of stress were assessed daily at the same time each morning. Measurements generated on Day 1, prior to TNBS injection, were used as the control. The total stool and stress score for the 4 days (total out of 8) following TNBS injection were combined and converted into a percentage. See Table 2 for details of scoring.

DESCRIPTION OF EMBODIMENTS

Figure 1:
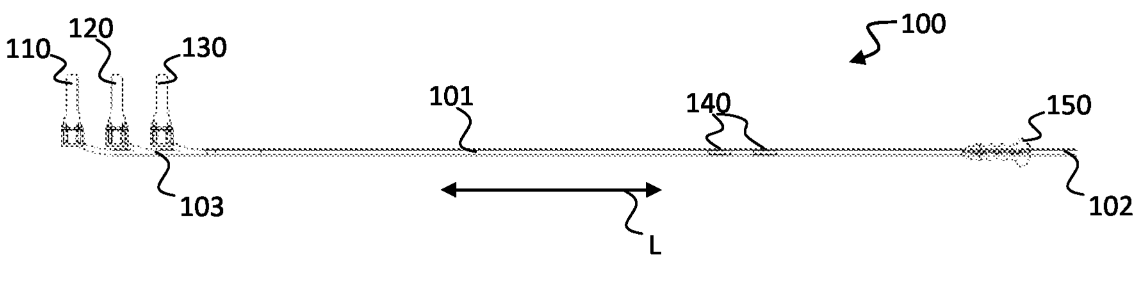
FIG. 1 shows a top view of a peripheral nerve electrode array according to an embodiment of the present disclosure.
Figure 2:
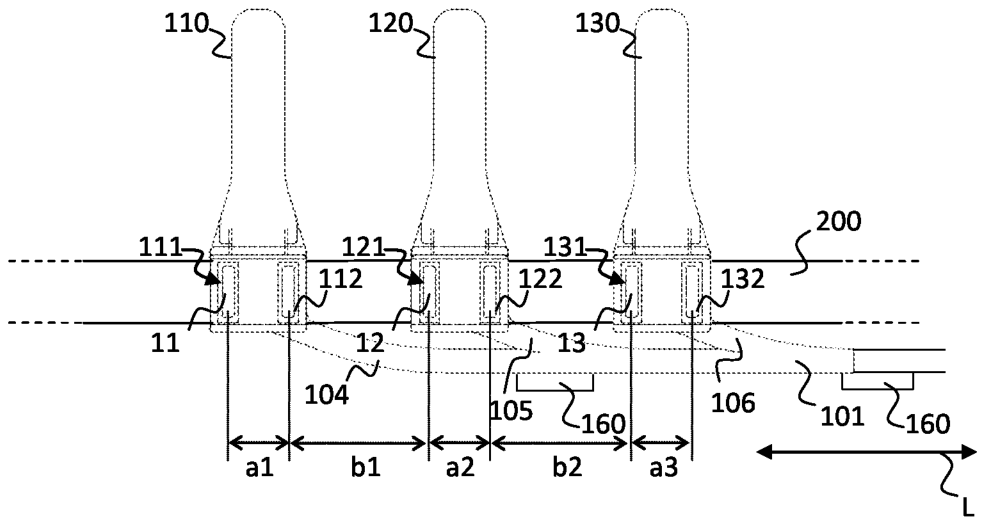
FIG. 2 shows a close up top view of a distal end region of the electrode array of FIG. 1.

A peripheral nerve electrode array 100 according to an embodiment of the present disclosure is illustrated in FIGS. 1 to 4*b*. The electrode array 100 includes a lead 101 that, at a proximal end 102 is connected or connectable to electrical stimulation apparatus and electrical monitoring apparatus (not shown) and at a distal end 103 includes electrodes for applying stimulation to a peripheral nerve and monitoring electrical response signals at the peripheral nerve. A close-up view of the distal end region of the lead 101 is shown in FIGS. 2 and 3.

At the distal end region, the lead 101 divides into three separate branches, a first branch 104, a second branch 105 and a third branch 106. Each branch has a separate electrode mounting device 110, 120, 130. Specifically, the first branch 104 has a first electrode mounting device 110, the second branch 105 has a second electrode mounting device 120 and the third branch 106 has a third electrode mounting device 130.

Each electrode mounting device 110, 120, 130 comprises a respective pair of electrodes 111, 121, 131. In particular: the first electrode mounting device 110 comprises a first pair of electrodes 111, the first pair of electrodes comprising two first electrodes 112 located proximate each other along a longitudinal axis of the electrode array; the second electrode mounting device 120 comprises a second pair of electrodes 121, the second pair of electrodes comprising two second electrodes 122 located proximate each other along the longitudinal axis of the electrode array; and the third electrode mounting device 130 comprises a third pair of electrodes 131, the third pair of electrodes comprising two third electrodes 132 located proximate each other along the longitudinal axis of the electrode array. The first, second and third mounting devices 110, 120, 130 are spaced from each other along the longitudinal axis of the electrode array 100 and thus the first, second and third pairs of electrodes 111, 121, 131 are also spaced from each other along the longitudinal axis of the electrode array 100. The second pair of electrodes 121 is located between the first and third pairs of electrodes 111, 131. The longitudinal axis of the electrode array 100 is represented by arrow L in FIGS. 1 and 2*a*. When the electrode array 100 is mounted to the peripheral nerve 200, the longitudinal axis L of the peripheral nerve 200 is substantially parallel to the longitudinal axis of the electrode array 100, at least at its distal end region 103.

As represented in FIG. 2, the first electrodes 112 are spaced from each other by a distance a1, the second electrodes 122 are spaced from each other by a distance a2 and the third electrodes 132 are spaced from each other by a distance a3, the distances a1, a2, a3 being in the longitudinal direction of the electrode array and generally from centre-to-centre of the respective electrodes. As also represented in FIG. 2*a*, the first and second pairs of electrodes 111, 121 are spaced from each other by a distance b1 and the second and third pairs of electrodes 121, 131 are spaced from each other by a distance b2, the distances b1, b2 being in the longitudinal direction of the electrode array and generally from centre-to-centre of the closest electrodes of the adjacent pairs of electrodes. In this embodiment, the distances between the electrodes within each pair of electrodes 111, 121, 131 is substantially equal, i.e. a1=a2=a3. Similarly, the distances between each pair of electrodes 111, 121, 131 is substantially equal, i.e. b1=b2. In this embodiment, the distances b1, b2 between the different pairs of electrodes 111, 121, 131 are each greater than the distances a1, a2, a3 between the electrodes within each pair of electrodes 111, 121, 131. The ratio between the distances a1, a2 and a3 and the distances b1 and b2 is between 1:1.5 and 1:3, and more specifically about 1:2.5 in this embodiment. In alternative embodiments, the distances a1, a2, a3 between each electrode within each pair of electrodes 111, 121, 131 may not be equal and/or the distances b1, b2 between the different pairs of electrodes 111, 121, 131 may not be equal. In some instances, such an asymmetric arrangement of electrodes may be desirable in view of anatomical and/or physiological conditions.

The electrode mounting devices are each adapted to mount on a peripheral nerve 200, as generally represented in FIG. 2, to bring the respective pair of electrodes 111, 121, 131 into secure electrical contact with the peripheral nerve 200. The electrodes 112, 122, 132 within each pair of electrodes 111, 121, 131 are elongated, their direction of elongation being transverse to the longitudinal axis of the electrode array 100 and therefore transverse to the longitudinal axis of the peripheral nerve 200. The electrodes 112, 122, 132 within each pair of electrodes 111, 121, 131 extend parallel to each other. The electrodes within each pair of electrodes 111, 121, 131 are positioned side by side both along the longitudinal axis of the electrode array 100 and along the longitudinal axis of the peripheral nerve 200 when mounted to the peripheral nerve 200.

In this embodiment, the electrode mounting devices 110, 120, 130 each have substantially identical structural features. For simplicity, the structural features of each electrode mounting device 110, 120, 130 are now described with reference to the first electrode mounting device 110 only.

The electrode mounting device 110 includes a first wing 113 and a second wing 114 that are adapted to extend on opposite sides of the peripheral nerve 200 and to be engageable with each other to form a loop. FIGS. 3 and 4*a* show the first and second wings 113, 114 in an open position and FIG. 4*b* shows the first and second wings 113, 114 in a closed position where the loop, generally indicated by arrow A, is formed.

The first wing 113 has a first cuff portion 115 and a first elongate extension portion 116 extending from the first cuff portion 115. The first cuff portion 115 has a first end 1151 and a second end 1152 and the first elongate extension portion 116 has a proximal end 1161 and a distal end 1162. The proximal end 1161 of the first elongate extension portion 116 is connected to the second end 1152 of the first cuff portion 115.

Similarly, the second wing 114 has a second cuff portion 117 and a second elongate extension portion 118 extending from the second cuff portion 117. The second cuff portion 117 has a first end 1171 and a second end 1172 and the second elongate extension portion 118 has a proximal end 1181 and a distal end 1182. The proximal end 1181 of the second elongate extension portion 118 is connected to the second end 1172 of the second cuff portion 117.

The first and second cuff portions 115, 117 are engageable with each other to form the loop as shown in FIG. 4*b*. To allow relative movement of the first and second cuff portions 115, 117 in order to achieve the engagement, the electrode mounting device has a pivot and specifically a flexible bearing 119 that connects the first ends 1151, 1171 of the first and second cuff portions 115, 117 together. The flexible bearing 119 enables relative rotation of the first and second cuff portions 115, 117.

As evident from e.g., FIGS. 3 to 4*b*, the length of each elongate extension portion 116, 118 is greater than the length of each of the first and second cuff portions 115, 117, the length directions extending transversely to the longitudinal axis L of the electrode array 100. In this embodiment, each elongate extension portion 116, 118 is in the form of an elongate tab. In this regard, each elongate extension portion 116, 118 can be formed of a substantially flat strip of material. However, other configurations of the elongate extension portions are possible.

As best seen in FIGS. 4*a* and 4*b*, each cuff portion 115, 117 has an inner surface 1153, 1173 with a semi-oblong profile. Thus, when the cuff portions are closed to form the loop A, the loop has an inner surface 1153, 1173 with an oblong profile, the oblong surface profile being of a suitable shape to contact an outer surface of the peripheral nerve 200. The inner surface 1153, 1173 may press against the nerve 200 to cause a compression of the nerve 200, which may shape the nerve 200 and increase a contact area between one or more electrodes exposed at the inner surface with the nerve 200. This may improve the interface characteristics between the nerve 200 and the electrodes.

In this embodiment, the first cuff portion 115 and the second cuff portion 117 are configured so that the distance therebetween when the cuff portions are closed to form the loop A is slightly smaller than a relevant size, or dimension (e.g. height, width or cross-sectional radius) of the peripheral nerve 200 to be placed therein. Thus, the loop A may achieve the desired deformation of the peripheral nerve 200 to encourage its interface with the relevant electrodes. The loop A may be shaped and configured (e.g. by material selection) to apply a pressure to the peripheral nerve 200 to reshape the nerve over time, wherein the pressure applied to the nerve is under a predetermined limit, such as approximately 30 mm Hg (approx. 4 kPa) during reshaping. It will be understood that other predetermined limits of pressure and/or force may be suitable.

In this embodiment, the second cuff portion 117 comprises the first electrodes 112, the first electrodes being exposed at the inner surface 1173 of the second cuff portion 117 and having a generally rectangular shape.

The electrode mounting devices 110, 120, 130 each include a locking mechanism to secure the first and second wings 113, 114, and specifically their first and second cuff portions 115, 117, in the looped configuration. In this embodiment, the locking mechanism is provided in part by an opening 1131 of the first wing 113, the opening 1131 being located at a transition between the first cuff portion 115 and the first elongate extension portion 116. The second wing 114 is movable to extend at least partly through the opening 1131, the movement bringing the second ends 1152, 1172 of the first and second cuff portions 115, 117 into engagement to form the loop A as shown in FIG. 4*b*. To assist this process, the first and second wings 113, 114, including their elongate extension portions 116, 118, are at least partly flexible.

The width of at least the second elongate extension portion 118 tapers towards its distal end 1182. The tapering is such that the distal end 1182 of the second elongate extension portion 118 is narrower than the opening 1131 of the first wing 113, enabling it to be readily inserted, distal end 1182 first, through the opening 1131. The proximal end 1181 of the second extension portion is wider than the second end 1172 of the second cuff portion 117 and wider than the opening 1131 of the first wing 113. The proximal end 1181 of the second extension portion 118 therefore defines a shoulder 1141 at a transition between the proximal end 1181 of the second elongate extension portion 118 and the second end 1172 of the second cuff portion 117. The material forming the shoulder 1141 is deformable in order to extend through the opening 1131. The natural shape of the shoulder 1141 is deformed to fit the shoulder 1141 through the opening 1131 and returns to its natural shape once through the opening 1131, preventing retraction back through the opening 1131 and therefore securing the first and second cuff portions 115, 117 in the loop.

Figure 5A:
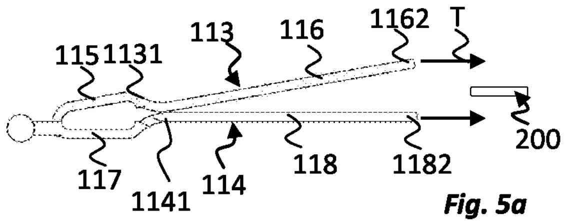
FIGS. 5*a* to 5*e* show steps taken to move the electrode mounting device of FIGS. 4*a* and 4*b* from the open to the closed configuration relative to a peripheral nerve.

A process of mounting the electrode mounting devices 110, 120, 130 to a peripheral nerve 200 is now described in more detail with reference to FIGS. 5*a* to 5*e* and 6*a* and 6*b*. The peripheral nerve 200 is surgically exposed at least at regions where electrical contact is to be made and the distal end region of the electrode array 100 is brought into proximity to the peripheral nerve 200, generally as represented in FIGS. 5*a* and 6*a*.

Figure 5B:
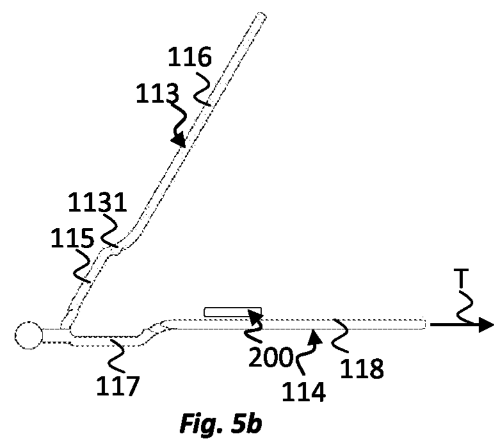
Figure 5C:
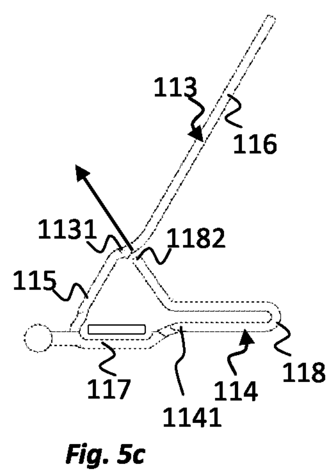
Figure 6A:
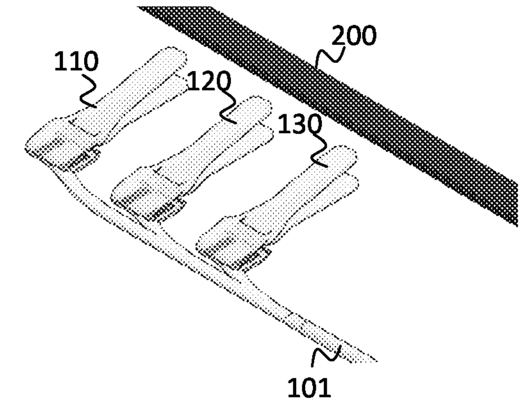
FIGS. 6*a* and 6*b* show perspective views of the distal end region of the electrode array of FIG. 1 in an open and closed configuration, respectively, relative to a peripheral nerve.

Subsequently, as represented in FIGS. 5*b* and 5*c*, the first and second elongate extension portions 116, 118 of each electrode device 110 are fed either side of the peripheral nerve 200, generally in a direction T that is perpendicular to the longitudinal axis of the peripheral nerve 200, until the first and second cuff portions 115, 117 are positioned either side of the peripheral nerve 200 as shown in FIG. 5*c*. Due to the relatively long lengths of the first and second elongate extension portions 116, 118, the first and second elongate extension portions 116, 118 can be easier to feed either side of the peripheral nerve 200, navigating past any potentially obstructive tissue. Moreover, due to their relatively long lengths, the first and second elongate extension portions 116, 118 can be relatively easy to take hold of once they have been fed either side of the peripheral nerve 200. By taking hold of and manipulating the first and second elongate extension portions 116, 118, a surgeon can move the first and second cuff portions 115, 117 to suitable positions either side of the peripheral nerve 200 and form the loop around the peripheral nerve 200.

Figure 5D:
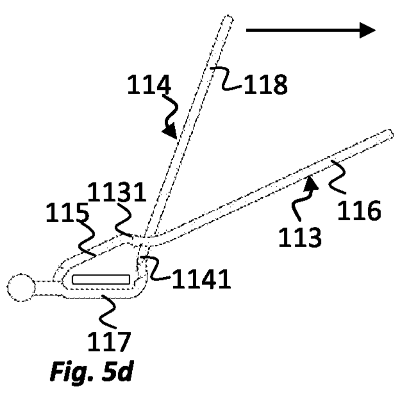
Figure 5E:
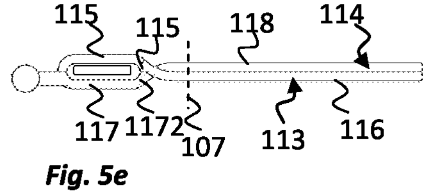
Figure 6B:
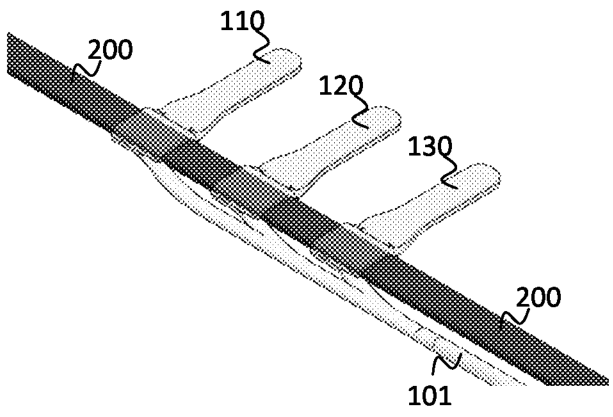

The forming of the loop around the peripheral nerve 200 is illustrated in FIGS. 5*c* to 5*e*. Initially, the distal end 1182 of the first elongate extension portion 118 is moved towards and into the opening 1131 of the first wing 113 (FIG. 5*c*). The first elongate extension portion 118 is then pulled through the opening 1131 (FIG. 5*d*) to a point where the second ends 1152, 1172 of the first and second cuff portions 115, 117 engage each other to form the loop A about the peripheral nerve 200 (FIGS. 5*e* and 6*b*). At this point, the first and second wings 113, 114 lock to each other by virtue of the shoulder 1141 of the second wing 114 squeezing through the opening 1131 and subsequently expanding, preventing retraction of the second elongate extension portion 118 back through the opening 1131.

After securing the first and second wings 113, 114 in the loop configuration, all or part of the first and/or second elongate extension portions 116, 118 can be removed from the electrode array 100. For example, using surgical snips or scissors, a surgeon may cut the first and second elongate extension portions 116, 118 along the line 107 indicated in FIG. 5*e*. In alternative embodiments, a region of weakness may be formed in the first and/or second elongate extension portions, e.g. at the line 107. The region of weakness may comprise a line of perforations, a tear notch, a score line or otherwise, enabling a user to tear off at least a part of the first and/or second elongate extension portions.

The first, second and third pairs of electrodes 111, 121, 131 are each selectively operable as a pair of stimulation electrodes, for applying an electrical stimulation signal to the peripheral nerve, and/or a pair of monitoring electrodes, for monitoring an electrical response signal at the peripheral nerve in response to an applied electrical stimulation signal.

Figure 7:
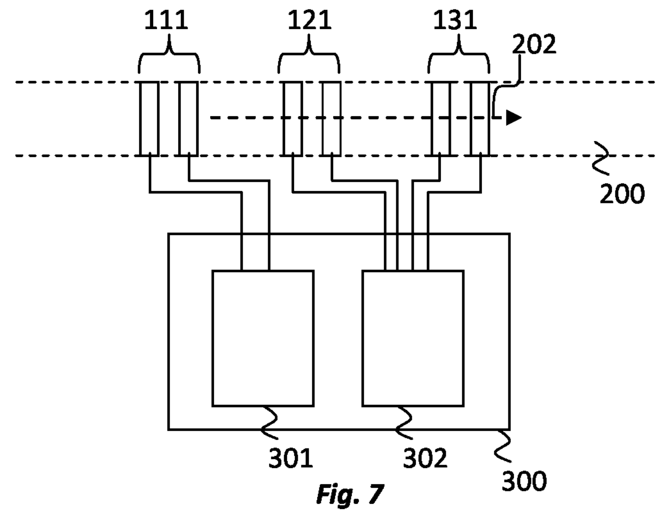
FIG. 7 shows a schematic illustration of electrical components of the electrode array of FIG. 1.

Referring to FIG. 7, in this embodiment, the first, second and third pairs of electrodes 111, 121, 131 are connected to control apparatus 300 that includes at least one electrical stimulation device 301 and at least one electrical monitoring device 302. The first pair of electrodes 111 is connected to the electrical stimulation device 301, the electrical stimulation device 301 generating electrical stimulation signals that are applied, via the first pair of electrodes 111, to the peripheral nerve 200. The second and third pair of electrodes 121, 131 are connected to the electrical monitoring device 302, the electrical monitoring device 302 receiving, from the second and third pairs of electrodes, electrical response signals generated at the peripheral nerve 200 in response to the applied electrical stimulation signals, the electrical response signals travelling in a direction 202 from the location of the first pair of electrodes 111.

In addition to the first, second and third pairs of electrodes, the electrode array 100 also includes return electrodes 140 (see FIG. 1) that can be used to check the quality of contact at the electrode-tissue interface for any of the first, second and third electrodes 112, 122, 132 individually and/or to check the state of the electrical circuit, including if there is a shorted or broken connection with any electrode. Moreover, the electrode array 100 includes an anchor 150 to anchor the electrode array 100 in a tissue wall, e.g. in an incision in a tissue wall adjacent the electrical stimulation location. Further, the electrode array 100 includes one or more tabs 160 (shown in FIG. 2 only) for securing the electrode array 110, e.g. a distal end region of the electrode array adjacent one or more the branches 104, 105, 106, to a surface of tissue adjacent the stimulation location. The tabs may be sutured to the tissue surface, for example. The electrode array 100 also includes conductive elements (not shown) such as conductive wires, e.g. platinum wires, that extend through the electrode array 100 and electrically connect to the electrodes.

In use, the second, monitoring pair of electrodes 121, may be placed as close as reasonably possible, along the longitudinal axis of the peripheral nerve, to the first, stimulating pair of electrodes 111, in order to precisely monitor the effects of the electrical stimulation at the peripheral nerve, including to pick up a 'C-fibre' response (e.g. as shown in FIG. 11*a* discussed further below). However, the present disclosure recognises that the closer the pair of monitoring electrodes is to the pair of stimulation electrodes, the greater risk that an electrical stimulation artefact will dominate the electrical response signal at least at an early response time when, for example, an 'A-delta fibre' response would be prevalent. By providing the third, further pair of monitoring electrodes 131, spaced further along the longitudinal axis of the peripheral nerve from the pair of stimulating electrodes 111 than the other pair of monitoring electrodes 121, this problem can be negated. If there is a stimulation artefact, of a size and duration that would significantly affect the quality of all or part of the recorded response, the further pair of monitoring electrodes 131 can provide a suitable backup or substitute, ensuring that monitoring of the response to electrical stimulation can still be successfully achieved, including for an 'A-delta fibre' response (e.g. as shown in FIG. 11*b* discussed further below).

Figure 8:
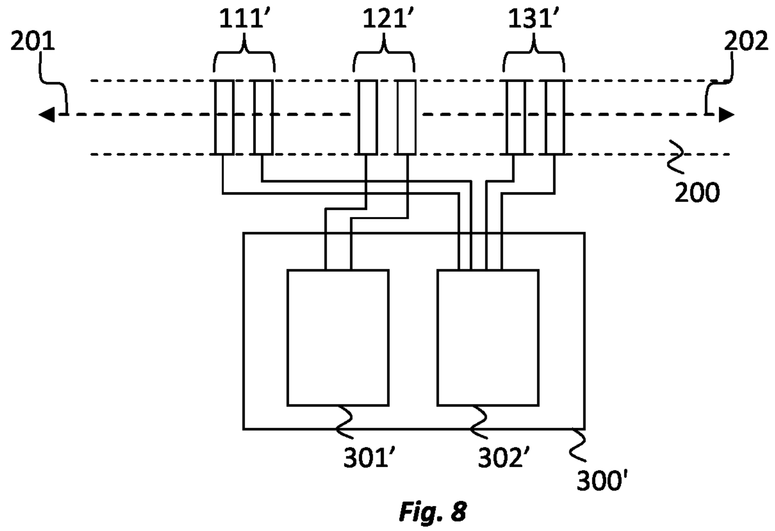
FIG. 8 shows a schematic illustration of electrical components of an electrode array according to an alternative embodiment of the present disclosure.

Referring to FIG. 8, in an alternative embodiment, the second pair of electrodes 121' is connected to the electrical stimulation device 301', the electrical stimulation device 301' generating electrical stimulation signals that are applied, via the second pair of electrodes 121', to the peripheral nerve 200. The first and third pair of electrodes 111', 131' are connected to the electrical monitoring device 302', the electrical monitoring device 302' receiving, from the first and third pairs of electrodes, electrical response signals generated at the peripheral nerve 200 in response to the applied electrical stimulation signals. The electrical response signals received by the first and third pairs of electrodes 111', 131' travel in first and second directions 201, 202 (e.g. afferent and efferent directions), respectively, from the location of the second pair of electrodes 121'.

Figure 9:
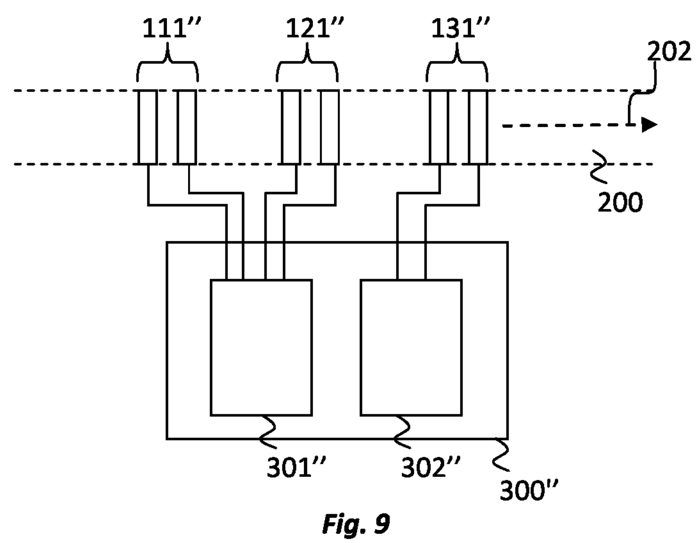
FIG. 9 shows a schematic illustration of electrical components of an electrode array according to another alternative embodiment of the present disclosure.

Referring to FIG. 9, in an alternative embodiment, the first and second pairs of electrodes 111", 121" are connected to the electrical stimulation device 301", the electrical stimulation device 301" generating electrical stimulation signals that are applied, via the first and second pairs of electrodes 111", 121", to the peripheral nerve 200. The third pair of electrodes 131" is connected to the electrical monitoring device 302", the electrical monitoring device 302" receiving, from the third pair of electrodes, electrical response signals generated at the peripheral nerve 200 in response to the applied electrical stimulation signals. By providing multiple electrical stimulation locations, the direction of electrical activity 202 may be more precisely controlled.

While the embodiments described above use three pairs of electrodes only, additional electrode pairs may be used. In accordance with this, referring to FIG. 10, in one embodiment, first, second, third, fourth and fifth pairs of electrodes 1110, 1210, 1310, 1410, 1510 are connected to control apparatus 300" that includes at least one electrical stimulation device 301'" and at least one electrical monitoring device 302". The third (middle) pair of electrodes 1310 is connected to the electrical stimulation device 301", the electrical stimulation device 301'" generating electrical stimulation signals that are applied, via the third pair of electrodes 1310, to the peripheral nerve 200. The first, second, fourth and fifth pairs of electrodes 1110, 1210, 1410, 1510 are connected to the electrical monitoring device 302", the electrical monitoring device 302" receiving, from the first, second, fourth and fifth pairs of electrodes, electrical response signals generated at the peripheral nerve 200 in response to the applied electrical stimulation signals. The first and second pairs of electrodes 1110, 1210 can monitor the electrical response in a first direction 201 (e.g. in an afferent direction) and the fourth and fifth pairs of electrodes 1410, 1510 can monitor the electrical response in a second direction 202 (e.g. in an efferent direction). The approach can provide advantages as set forth above, including to manage stimulation artefacts when monitoring of electrical response signals in two directions.

The present disclosure further relates to methods and systems for treating or preventing a chronic inflammatory condition in a human subject, e.g., a chronic inflammatory condition such as inflammatory bowel disease (IBD), by stimulating the CAV nerve through two or more implanted electrodes at a site below the cardiac branches and above the hepatic-celiac branches of the vagus nerve. This location for vagus nerve stimulation is advantageous in providing stimulation of disease-relevant target organs including small intestine, the upper half of the colon, and spleen, while avoiding off-target organs associated with previously used sites for vagus nerve stimulation such as the larynx, heart, and lungs. While not wishing to be bound by theory, it is believed that stimulation of the vagus nerve reduces both the local enteric TNF alpha levels (via cholinergic efferent production of acetylcholine) and systemic levels (via actions to the spleen) associated with IBD and other chronic inflammatory conditions thereby leading to a therapeutic or prophylactic effect on a chronic inflammatory condition such as an IBD. In addition, stimulation of the anterior or posterior CAV nerve also stimulates afferent input into hypothalamic regions, which is believed to exert anti-inflammatory and immunosuppressive affects via systemic glucocorticoid release.

The term "administering a therapeutic agent," as used herein, refers to any of a range of related activities that ultimately result in introducing a therapeutic agent into a patient undergoing any of the treatment methods disclosed herein. Such activities include, prescribing a therapeutic agent for use in a method disclosed herein, whereby the subject to be treated self-medicates with the prescribed agent; and directly medicating, or instructing a second party to directly medicate the subject with a therapeutic agent by any suitable route (e.g., oral, intravenous etc.).

The term "electrical stimulation device," as used herein, refers to a device that utilises a power source to provide an electrical stimulation having pre-determined stimulation settings including, but not limited to, pulse phase number, inter pulse phase gap, pulse intensity, pulse duration (width), stimulation frequency, duty cycle, stimulation duration, and stimulation current. The electrical stimulation from the electrical stimulation device is applied to a target nerve, e.g., the CAV nerve, through two or more electrodes operatively coupled to the electrical stimulation device, and in contact with the target nerve.

The term "preventing," as used herein, refers to an intervention in a subject for the purpose of reducing the subject's risk of developing a chronic inflammatory condition or reducing the risk of the subject having a relapse of an active chronic inflammatory condition.

The term "providing" with reference to a "therapeutically effective stimulation," as used herein encompasses any one of the following in regard to a subject suffering from or at risk of a chronic inflammatory condition: implanting or instructing medical personnel to implant in the subject at a site below the cardiac branches and above the hepatic-celiac branches of the vagus nerve two or more electrodes, or any device comprising the two or more electrodes, positioned to provide the therapeutically effective stimulation, to the anterior CAV nerve or posterior CAV nerve (or both); configuring (e.g., setting patient-specific stimulation parameters) or instructing medical personnel or the subject to configure the two or more electrodes or the device to stimulate at least one of the anterior CAV nerve or the posterior CAV nerve; and initiating or terminating, or instructing medical personnel or the subject to initiate or terminate, a stimulation regimen through the two or more implanted electrodes device in the course of stimulation of the anterior or posterior CAV nerve.

The term "treating," as used herein, refers to an intervention in a subject for the purpose of reducing a pathophysiology or one or more of the symptoms of an active chronic inflammatory condition.

"a therapeutically effective stimulation," as used herein, refers to a level of stimulation of a branch of the CAV nerve that reduces a pathophysiology or one or more of the symptoms experienced by the subject, or reduces a subject's risk of developing a chronic inflammatory condition or having a relapse of an active chronic inflammatory condition. In some embodiments a reduction in a pathophysiology, a symptom, or a risk can be at least a 10% to about a 100% reduction, e.g., 15%, 20%, 30%, 40%, 50%, 60%, 70%, 80%, 90%, 95%, or another percent reduction in a pathophysiology or one or more symptoms experienced by the subject being treated for a chronic inflammation condition.

Described herein is a method for treating or preventing a chronic inflammatory condition in a human subject in need thereof, where the method includes providing a therapeutically effective electrical stimulation to a branch of the CAV nerve through two or more previously implanted electrodes at a site located below the cardiac branches and above the hepatic-celiac branches of the vagus nerve.

In some embodiments the just-mentioned method is only provided to a subject with an active chronic inflammatory condition (i.e., with evident symptoms), as a method of treating a chronic inflammatory condition such as IBD. In other embodiments the above-mentioned method is provided to a subject that has previously experienced an active inflammatory condition, but is not experiencing active symptoms (or only minor symptoms) for the purpose of preventing (a relapse) of a chronic inflammatory condition.

Also provided herein is method for preventing or treating a chronic inflammatory condition in a human subject in need thereof, comprising implanting in the subject two or more stimulating electrodes at a site below the cardiac branches and above the hepatic-celiac branches of the vagus nerve, wherein such electrodes are configured to provide a therapeutically effective stimulation of a branch of the CAV nerve to treat or prevent the chronic inflammatory condition. Implanted electrodes are brought into contact with a branch of the CAV nerve in order to apply electrical stimulation.

Described herein is the use of two or more electrodes for treating or preventing an inflammatory bowel disease, wherein the two or more electrodes deliver stimulation to the anterior or posterior CAV nerve at a site below the cardiac branches and above the hepatic-celiac branches of the CAV nerve. In some embodiments suitable electrodes are monopolar electrodes. In other embodiments the electrodes are bipolar electrodes. In further embodiments the electrodes are tripolar electrodes.

Figure 15:
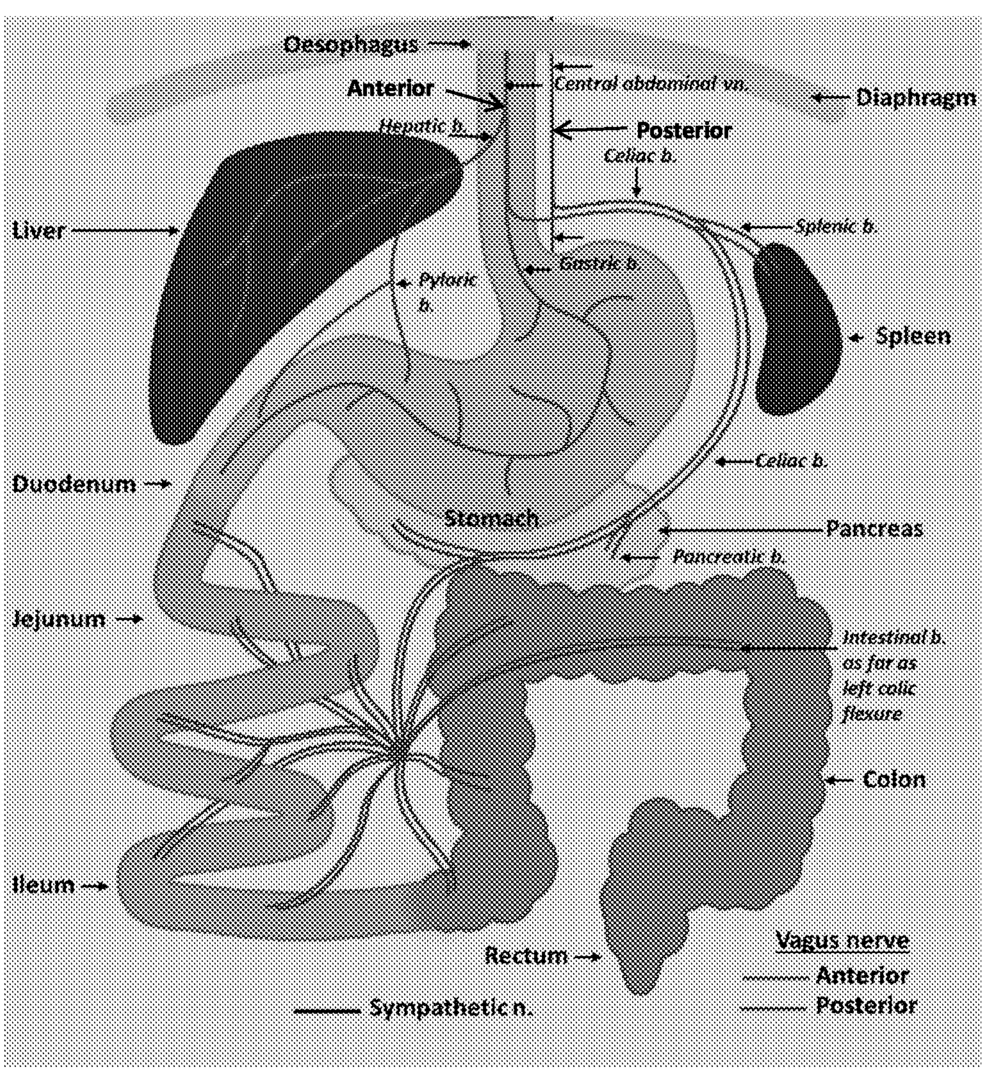
FIG. 15 shows a schematic view of implantable electrode placement and stimulation site on the CAV nerve according to an embodiment of the present disclosure.
Figure 17:
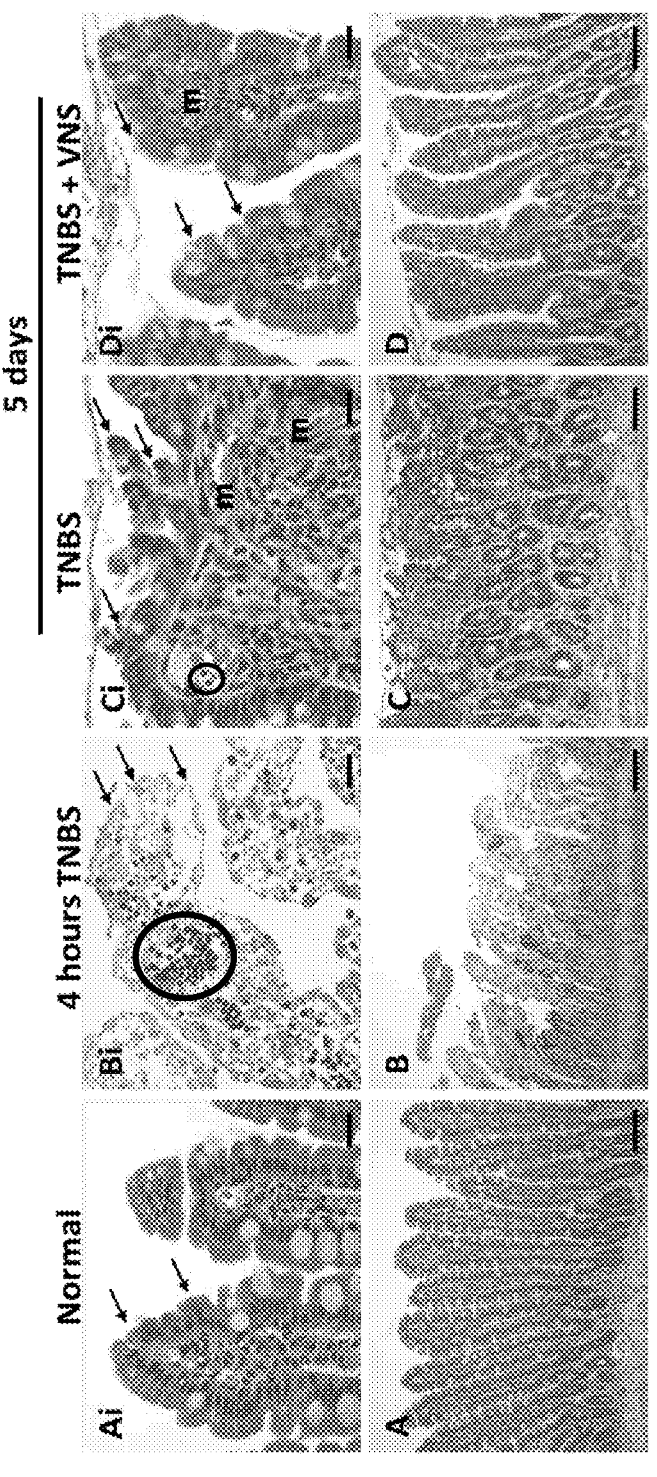
FIG. 17 shows VNS alleviated histological damage in gut tissue. A: Normal ileum (A, Ai) had undamaged, intact surface epithelium (arrows, Ai). B, Bi: At 4 hours following TNBS injection (the time that active VN stimulation was applied) extensive epithelial cell loss (arrow, B) and leukocyte infiltration (circle) was observed. C, Ci: At 5 days following TNBS injection, there was extensive damage to villi (Ci, arrows), leukocyte infiltration in venules (circle) and micro-haemorrhages (m) in unstimulated tissue. Villi architecture were severely disrupted. D, Di: In VN stimulated tissue, signs of histological damage was reduced. Villi were long and undamaged. Surface epithelium were intact (arrows) although some microhemmorhages were observed (m). Scale bars in A-D: 100 μm; in Ai-Di: 20 μm.

In some preferred embodiments the two or more implanted electrodes are located in proximity to a branch of the CAV nerve just below the diaphragm. For one exemplary embodiment, the anatomical position for electrode implantation and stimulation of anterior or posterior CAV nerve is schematically illustrated in FIG. 15.

Generally, the methods provided herein will provide therapeutic benefit in the absence of or at least a reduced level of side effects associated with vagus nerve stimulation at other sites. Such side effects that are avoided or reduced in the methods described herein include, but are not limited to voice changes, hoarseness, throat pain, cough, headaches, chest pain, breathing problems, and difficulty swallowing. Further, the treatment methods described herein are likely safer than, e.g., cervical vagus nerve stimulation, for treatment of IBD patients that also suffer from heart problems, difficulty swallowing, or pulmonary conditions.

In some embodiments the treatment method will further encompass the step of surgically implanting in a subject to be treated the two or more electrodes required for therapeutic stimulation of anterior or posterior CAV nerve to treat a chronic inflammatory condition such as an IBD.

Chronic inflammatory conditions that can be treated by the methods disclosed herein include, but are not limited to, an inflammatory bowel disease (IBD), non-alcoholic steatohepatitis, pancreatitis, asthma, osteoarthritis, rheumatoid arthritis, ankylosing spondylitis, chronic active hepatitis, chronic peptide ulcer, lupus erythematosus, Grave's disease, and psoriasis.

In preferred embodiments the condition to be treated is an inflammatory bowel disease including, Crohn's disease, ulcerative colitis. In some preferred embodiments the condition to be treated is ileo-caecum Crohn's Disease. Where the type of IBD to be treated is Crohn's disease, the Crohn's disease subtype is selected from the group consisting of ileocolitis, ileitis, gastroduodenal Crohn's disease, jejunoileitis, and Crohn's (granulomatous) colitis. Where the type of IBD to be treated is ulcerative colitis, the subtype of ulcerative colitis is selected from the group consisting of ulcerative proctitis, proctosigmoiditis, left-sided colitis, and pan-ulcerative colitis.

Methods for diagnosis and prognosis of chronic inflammatory conditions, such as IBD, are established in the art.

In various embodiments, where the subject to be treated is suffering from IBD, treatment results in improvement of one or more endpoints including, but not limited to: transmural neutrophil infiltration, eosinophil infiltration into circular muscle, eosinophil infiltration in longitudinal infiltration in circular muscle, eosinophil infiltration in submucosa, eosinophil infiltration in mucosa, CD33+ T-cell infiltration in circular muscle, CD33+ T-cell infiltration in longitudinal muscle, CD33+ T-cell infiltration in sub-mucosa, and CD33+ T-cell infiltration in mucosa, circulating C-reactive protein levels, and stool production. Additional suitable disease activity indices and assessment methods include, but are not limited to, assessment of weight loss, stool quality, pain; endoscopic examination, molecular analysis including analysis of calprotectin or blood content in faeces, assessment of circulating inflammatory cytokines such as TNF-alpha, IL-6, IL-1, C reactive protein (CRP), mucosal biopsy, magnetic resonance imaging (MRI), and mannitol and lactose gut permeability assessment. In some embodiments, particularly where the subject is suffering from an IBD, an IBD Disease Activity Index is used to assess the status of the subject. Components of the IBD Disease Activity Index include: number of liquid or soft stools each day for seven days; abdominal pain; subjective assessment of general well-being; presence of complications; taking Lomotil or opiates for diarrhoea; presence of an abdominal mass; haematocrit; and percentage deviation from standard weight. In some embodiments a subject to be treated for and IBD has an IBD Disease Activity Index of at least about 220-450.

Such an improvement is from at least about a 10% to about a 100% improvement, e.g., 15%, 20%, 25%, 30%, 40%, 50%, 60%, 70%, 80%, 90%, or another percent improvement from at least about 10% to 100% of one of the foregoing endpoints relative to those observed prior to treatment of the subject.

In some embodiments the anterior branch CAV nerve is to be stimulated. In other embodiments the posterior CAV nerve is to be stimulated. In yet other embodiments, both the anterior and posterior CAV nerves are to be stimulated. In some embodiments, when both anterior and posterior CAV nerves are to be stimulated, the stimulation can be provided substantially simultaneously. In other embodiments, the stimulation can be provided at different times. In some embodiments the stimulation regimen provided to each of anterior and posterior CAV nerves can be the same. Alternatively, the stimulation regimen provided to anterior and posterior CAV nerves can be different.

In some embodiments, following stimulation of the CAV, an evoked response is to be recorded in the CAV. Confirmation of evoked responses in the CAV, particularly in the C fibres, can serve as a useful indication that the stimulation parameters are adequate. In some embodiments, measurement of one or more evoked response properties in the CAV can be utilized to guide subsequent CAV stimulation parameters. Optionally, the measured CAV evoked response properties can serve as an input to adjust dynamically CAV stimulation parameters over the course of a treatment regimen, which is also referred to as a "closed loop" configuration.

In some embodiments suitable stimulation is administered as a biphasic pulse having the following ranges of stimulation parameters in any combination: (i) a pulse width of about 100 µsec to about 600 µsec, e.g., 120 µsec, 150 µsec, 175 µsec, 200 µsec, 220 µsec, 250 µsec, 300 µsec, 310 µsec, 320 µsec, 350 µsec, 375 µsec, 400 µsec, 425 µsec, 450 µsec, 500 µsec, 525 µsec, 550 µsec, 575 µsec or another pulse width from about 100 µsec to about 600 µsec;

(ii) an interphase gap of about 25 µsec to about 100 µsec, e.g., 30 µsec, 40 µsec, 50 µsec, 60 µsec, 80 µsec, 90 µsec, or another interphase gap of about 25 µsec to about 100 µsec;

(iii) a stimulation frequency of about 0.1 Hertz to about 40 Hertz (Hz), e.g., 0.2 Hz, 0.3 Hz, 0.4 Hz, 0.5 Hz, 0.7 Hz, 1 Hz, 2 Hz, 3 Hz, 4 Hz, 7 Hz, 8 Hz, 12 Hz, 14 Hz, 16 Hz, 18 Hz, 20 Hz, 25 Hz, 27 Hz, 30 Hz, 32 Hz, 35 Hz, 38 Hz, or another stimulation frequency from about 0.1 Hz to about 40 Hz;

(iv) a stimulation duration of about 10 seconds to 5 minutes, e.g., 20 seconds, 30 seconds, 40 seconds, 50 seconds, 60 seconds, 80 seconds, 90 seconds, 110 seconds, 2 minutes, 2.5 minutes, 3 minutes, 3.5 minutes, 4 minutes, 4.5 minutes or another stimulation duration from about 10 seconds to about 5 minutes; and (v), a stimulation current of about 0.2 mA to about 10 mA, e.g., about 0.3 mA, 0.5 mA, 0.8 mA, 1.0 mA, 1.5 mA, 1.7 mA, 2.0 mA, 2.5 mA, 3.0 mA, 4.0 mA, 5.0 mA, 6.0 mA, 7.0 mA, 8.0 mA, 8.5 mA, or another stimulation current from about 0.2 mA to about 10 mA.

In some embodiments the duty cycle for suitable stimulation ranges from about 5% to about 100%, e.g., 10%, 20%, 30%, 40%, 50%, 70%, 80%, 90%, or another duty cycle value from about 5% to about 100%.

In some preferred embodiments, the stimulation delivers biphasic pulses having a 200 μsec pulse with a 50 μsec pulse interphase gap at a frequency of 10 Hertz, and with a stimulation current of about 1.6 mA, for a duration of 30 seconds. In some embodiments, additional stimulation of the CAV nerve is provided, e.g., as a series of repeated stimuli. In some embodiments, the stimulation parameters for each stimulus in a series will be the same. Alternatively, stimulation parameters can be varied for each stimulus.

In some embodiments a therapeutically effective electrical stimulation is provided to the subject multiple times, which may increase the overall efficacy of a treatment for the subject. In some embodiments, the therapeutically effective electrical stimulation is provided about 2 times per day to about 10 times per day, 3 times per day, 4 times per day, 5, times per day, 6 times per day, 7 times per day, 8 times per day, 8 times per day, or 9 times per day. In some embodiments, the total period of a given bout of treatment may range from about one week to about one year, e.g., 2 weeks, 3 weeks, 4 weeks, 5 weeks, 2 months, 3 months, 4 months, 5 months, 6 months, 7 months, 8 months, 9 months, 10 months, 11 months, or another total treatment period from about one week to about one year. In some embodiments the treatment method comprises a period of about six months stimulation with 200 μsec biphasic pulse with a stimulation current of 1.6 mA for a duration of 30 seconds followed by five minutes of no stimulation before reinitiating electrical stimulation with the same parameters. This duty cycle is run continuously (24 hours a day).

The skilled person will appreciate that stimulation parameters, their variation, the need for multiple stimulation regimens, and the overall treatment period in a treatment method described herein are determined in view of a number of considerations including, but not limited to, therapeutic responsiveness of the subject to one or more stimulation regimens; and the severity of observed side effects, if any, during the course of treatment.

In some embodiments two or more implanted electrodes are to be used. In other embodiments three or more implanted electrodes are to be used. In some preferred embodiments four implanted electrodes are used. In preferred embodiments the two or more implanted electrodes comprise at least one stimulating electrode and one recording electrode.

In some embodiments the two or more implanted electrodes used are bipolar cuff electrodes, which can be used for stimulation of and/or recording of evoked responses from the CAV. In some embodiments stimulating electrodes are provided as part of an implanted electrode array. In preferred embodiments such an electrode array includes both stimulating and recording electrodes, as illustrated in FIG. 16.

In preferred embodiments electrical stimulation through the two or more implanted electrodes is provided by means of an electrical stimulation device, which utilises a power source to generate electrical stimulation signals based on predetermined stimulation settings, to apply an electrical stimulation via two or more stimulating electrodes to anterior or posterior CAV nerves. In preferred embodiments the stimulation device is adapted to be communicatively coupled to a computing device storing or having access to a plurality of electrical stimulation settings, and a user interface to enable authorised selection of at least one of the electrical stimulation settings (e.g., pulse width, pulse frequency, and stimulation duration). In some embodiments the computing device is integrated into the electrical stimulation device. In other embodiments the computing device is separate from the electrical stimulation device, though it is still communicatively coupled to the electrical stimulation device, e.g., through a wireless system.

In preferred embodiments an electrical stimulation device to be used in the disclosed methods is to be implanted in the human subject to be treated. In other embodiments the electrical stimulation device is not to be implanted, but rather carried on the body of the human subject, e.g., via affixture to the subject's skin.

Suitable implantable power sources for implantable electrical stimulation devices, include, e.g., lithium batteries, thermoelectric generators, electromagnetic generators, and electrostatic generators. In some preferred embodiments the implanted power source is a battery. General requirements of suitable batteries for implanted electrodes include high safety, reliability and volumetric energy density, long service life, and an indication of discharge status.

Where the electrical stimulation device to be used is not to be implanted, but is external, suitable power sources include, but are not limited to batteries, optical chargers, ultrasonic transducers, and inductive coupling devices.

In some embodiments a therapeutically effective stimulation of the CAV nerve is applied via an implanted electrode array. In some preferred embodiments a suitable electrode array placed in operable contact with anterior CAV nerve or posterior CAV nerve comprises one or more pairs of electrodes.

The pairs of electrodes apply an electrical stimulation signal to the CAV nerve and/or monitor (e.g. recording) evoked and/or spontaneous responses in the CAV nerve. The electrode array may comprise or may be connected to one or more electrical stimulation devices, comprising a processor, that generate the electrical stimulation signals to apply, via the respective pair(s) of electrodes, to the CAV nerve. The electrode array may also comprise or may be connected to one or more monitoring devices that receive, from the respective pair(s) of electrodes, evoked and/or spontaneous response signals and then process the response signals for further analysis. Exemplary embodiments of the use of such arrays are illustrated in FIG. 16.

Also described herein is a system for configuring an electrical stimulation device in conjunction with any of the methods described herein, the system comprising: two or more electrodes implanted in a human subject to be treated at a site below the cardiac branches and above the hepatic-celiac branches of the vagus nerve, and configured to stimulate the anterior CAV nerve or the posterior CAV nerve; a computing device storing or having access to a plurality of electrical stimulation settings and comprising a user interface to enable authorised selection of at least one of the electrical stimulation settings for provision of electrical stimulation by the stimulation device according to the one setting; and the stimulation device communicatively coupled to the computing device to receive and store the selected electrical stimulation setting, the stimulation device being of a size to be readily implantable or carried on a body and configured to selectively provide current to the at least one implanted electrode according to the at least one electrical stimulating setting. In some embodiments the two or more electrodes in the system are provided in an electrode array.

Also contemplated is a kit to be used in any of the methods provided herein according to provided instructions, the kit comprising: two or more implantable electrodes adapted to stimulation of the anterior CAV nerve or the posterior CAV nerve; a computing device for storing or having access to a plurality of electrical stimulation settings and comprising a user interface to enable authorised selection of at least one of the electrical stimulation settings for provision of electrical stimulation by the stimulation device according to the one setting; and a stimulation device communicatively adapted for coupling to the computing device to receive and store the selected electrical stimulation setting, the stimulation device being of a size to be readily implantable or carried on a body and configured to selectively provide current to the at least one implantable electrode according to the at least one electrical stimulating setting. In some embodiments the two or more implantable electrodes are provided in an electrode array.

In some embodiments, where the method further includes detecting one or more evoked responses in the CAV, a monitoring device is used to detect and amplify a signal from one or more recording electrodes in contact with the stimulated CAV. Preferably, such monitoring devices are implanted monitoring devices.

In some embodiments the treatment or prevention methods provided herein further include administering to a subject suffering from a chronic inflammatory condition, and particularly for an IBD, a therapeutic effectively effective amount of a therapeutic agent for treating the chronic inflammatory condition. In some embodiments the therapeutic agent to be administered is an anti-inflammatory drug, an immunosuppressant, an antibiotic, or a combination thereof. Such combination therapy may be advantageous over the corresponding monotherapies, particularly with regard to therapeutic agents alone, as these may require higher doses and may be effective for more limited periods as compared to administration in combination with the treatment methods presented herein. In some embodiments a therapeutically effective dose of the therapeutic agent to be administered in combination with CAV nerve stimulation is reduced by about 10% to about 90% relative to a therapeutically effective dose of the therapeutic agent administered as a monotherapy, e.g., a reduction of about 15%, 18%, 20%, 25%, 30%, 40%, 50%, 55%, 60%, 70%, 75%, 80%, 85%, or another percent reduction in therapeutic agent dose from about 10% to about 90%.

Suitable anti-inflammatory drugs include, but are not limited to, corticosteroids, aminosalicylates (e.g., mesalamine, balsalazide, olsalazine, and anti-tumor necrosis factor-alpha antibodies.

Suitable immunosuppressants include, but are not limited to, azathioprine, mercaptopurine, cyclosporine, and methotrexate.

Suitable antibiotics include, but are not limited to, ciprofloxacin, clarithromycin,

Example 1

An electrode array consisting of a stimulating electrode pair (pair 1-2) and two monitoring electrode pairs (pair 3-4 and pair 5-6) were implanted and attached in a spaced apart configuration to the vagus nerve of a sheep. In the spaced apart configuration, adjacent electrode pairs were separated by about 10 mm (e.g. b1 or b2 in FIG. 2), and bipolar electrodes in a pair were separated from each other by about 2 mm (e.g. a1, a2 or a3 in FIG. 2). Electrical signals were applied as bipolar biphasic stimulation to the nerve by the stimulating electrode pair (10 Hz, 1 mA, 200 μs pulse width, 50 μs interphase gap). A recording (FIG. 11*a*) was made of an electrically evoked compound action potential (ECAP) received by the monitoring electrode pair (3-4) that was closest (10 mm separation) to the stimulating electrode pair (pair 1-2) and a recording (FIG. 11*b*) was made of an ECAP received by the monitoring electrode pair (5-6) that was farthest (20 mm separation) from the stimulating electrode pair (pair 1-2).

FIG. 11*a* shows a 'C-fibre' latency response in the ECAP for the closest monitoring electrode pair approximately 15 ms after the stimulation artefact (SA). FIG. 11*b* shows an 'A-delta fibre' latency response approximately 1.5 ms after stimulation, but no clear 'C-fibre' latency response after the stimulation. The box inset is a close-up of the 'A-delta fibre' latency response.

Example 2

In another example, electrode arrays comprising of a stimulating electrode pair (E1-E2) and two monitoring electrode pairs (E3-E4 and E5-E6) was implanted onto the vagus nerve of the lower thorax in five animals (sheep) for a study over approximately 3 months. The electrode array featured three electrode mounting devices, each mounting device having a pair of platinum (99.95%) electrodes. Each electrode was embedded in a medical grade silicone elastomer carrier and had an exposed surface area of 2.5 mm×0.6 mm (about 1.5 $mm^2$). Adjacent electrode pairs were separated by 10 mm (b1 or b2 in FIG. 2), and electrodes in each pair were separated from each other by 2 mm (a1, a2 or a3 in FIG. 2). In general, the electrode array was similar to that described above with reference to FIG. 2, wherein electrodes E1-E2 correspond to the first electrodes 112, electrodes E3-E4 corresponding to the second electrodes 122 and electrodes E5-E6 correspond to the third electrodes 132.

A chronic stimulation program was commenced one month after the implantation of the electrode arrays in sheep. Charge balanced biphasic current pulses of 0.4 μC/phase were continuously delivered generating a charge density of 27 $\mu C/cm^2$/phase. The stimulus was delivered at 30 pulses per second (pps, or Hz) using a 30 seconds ON, 150 seconds OFF duty cycle at 2 mA current.

ECAPs were recorded for the sheep weekly in order to monitor neural function. Biphasic current pulses (10 Hz, 200 μs per phase, 50 μs interphase gap) were used to stimulate bipolar electrodes E1-E2. Neural responses were recorded from electrodes E3-E4 (10 mm from the site of stimulation) or E5-E6 (20 mm from the site of stimulation) in order to record slow and fast conduction ECAPs respectively without significant contamination from the electrical artefact. Recordings were made at intensity intervals from below threshold to 2.0 mA in 0.1 mA steps. Recordings were made at a rate of 100 kHz, filtered (high pass: 200 Hz; low pass: 2000 Hz), amplified ($\times 10^3$) and 50 presentations were averaged for each response. The ECAP threshold was defined as the minimum stimulus intensity producing a response amplitude of at least 1 μV in both recordings within a latency window of 4-8 ms following the stimulus. It should be understood that shorter pulse widths may produce shorter artefacts (although this may not always be the case). Therefore longer pulse widths may be used, in which case they may be accompanied by arrangement of arrays with larger b1 & b2 values than some of those described above.

Figure 12:
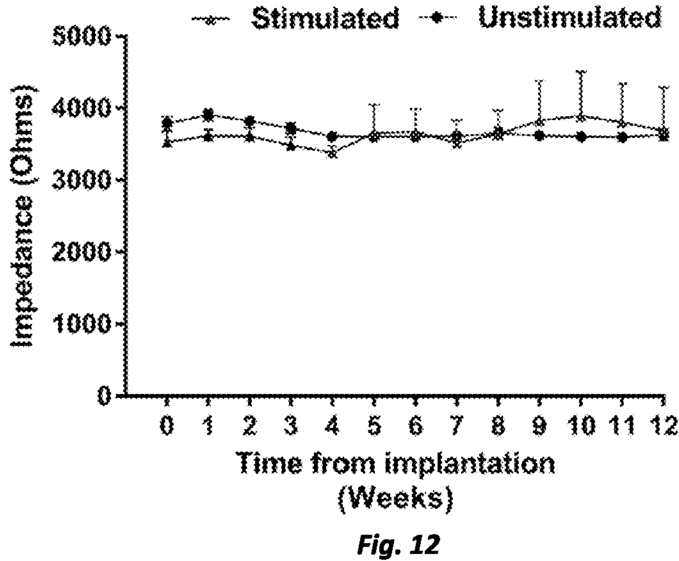
FIG. 12 shows electrode impedance recorded weekly during the implantation period for all electrodes in an Example 2 (data shows mean impedance +SEM)

Neural thresholds remained well below the stimulus levels used for chronic stimulation (2 mA, 200 μs pulse width), thereby confirming that the vagus nerve was stimulated at suprathreshold levels for the duration of the stimulus program. It is also noted that as detailed elsewhere in the present application, the electrophysiologically determined stimulation thresholds remained stable throughout the implantation period, as shown in FIG. 12. A clinical pathologist reported no damage to nerve fascicles due to the implant and/or electrical stimulation, and no evidence of granulation tissue or the infiltration of acute inflammatory cells.

A summary of sheep and stimulation used in this example is tabulated below in Table 1:

TABLE 1

| Sheep | Implantation duration (weeks) | Stimulated electrodes | Charge per phase (nC) | Total switch on time (hours) | Adverse events | Electrode region at autopsy |
|---|---|---|---|---|---|---|
| VNS 1 | 12.8 | E1-E2 | 400 | 984 | None | Benign tissue fibrosis; no infection |
| VNS 2 | 13.6 | E1-E2 | 400 | 1524 | None | Benign tissue fibrosis; no infection |
| VNS 3 | 13.1 | E1-E2 | 400 | 1800 | None | Benign tissue fibrosis; no infection |
| VNS 4 | 12.1 | E1-E2 | 400 | 1404 | None | Benign tissue fibrosis; no infection |
| $VN_c5$ | 7.9 | N/A | N/A | N/A | Yes-event not related to device | Less mature tissue fibrosis; no infection |

Each electrode array was recovered from the sheep and analysed at the end of the study period to evaluate suitability of the electrode array for chronic implantation of the vagus nerve.

In this example, all electrodes remained functional throughout the implantation period, and no significant difference was noted between the impedance of chronically stimulated (triangular symbols) and unstimulated electrodes (circular symbols) over the implantation period (P=0.37). ECAP thresholds remained well below stimulation levels, and did not significantly increase over the implantation period, as shown in FIG. 12. In FIG. 12, data show mean common ground impedance+S.E.M. While all error bars have been plotted, some are obscured by the symbols.

Examination of the electrode array in vivo showed that a thin fibrous tissue encapsulation had formed around the array, and there was no distortion (i.e. twisting) of the vagus nerve. The tissue encapsulation was restricted to the vicinity of the array, and did not spread from this area and affect adjacent tissues. Attachment of the electrode array had not caused any macroscopic damage to the nerve, and blood vessels were typically observed running longitudinally along the implanted vagus nerve. No irritation, haemorrhaging or haematomas were observed within adjacent tissue (oesophagus, lung and pericardium).

The mounting devices including the second pair of electrodes (E4-E5), and with the vagus nerve contained within, was embedded in epoxy resin and grinded to expose a cross-section for analysis. Analysis of the cross-section was carried out. By embedding and sectioning electrodes E3 and E4 together with the vagus nerve contained within these electrodes, we were able to examine the electrode neural interface in some detail. The vagus nerve and its fibrous tissue capsule were identified within the cavity formed around the nerve by the cuff electrode. In all animals examined (n=5), the nerve and its associated tissue capsule did not always occupy the entire cavity (data not shown). While we cannot dismiss the possibility of tissue shrinkage, these results indicate that the nerve may not always form a tight interface with the electrodes. However, the cross-sectional profile of the nerve reflects the longitudinal distortion observed in the histological sections (data not shown). Inspection of the region of the cavity in each animal showed no evidence of tissue adhesions, cellular debris or an accumulation of inflammatory cells. The platinum electrode was evident at the interface between the silicone carrier and the cavity. The vagus nerve was positioned approximately 100-200 μm from the electrode and this was typical for all animals examined using this technique.

Figure 13:
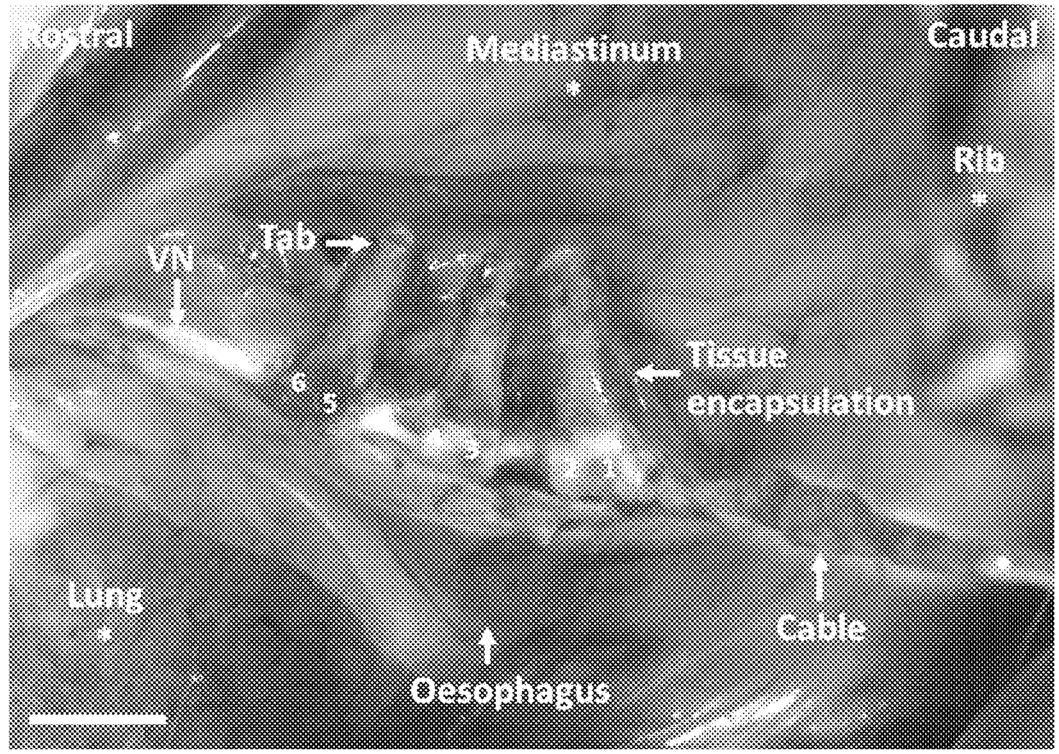
FIG. 13 shows the typical gross tissue response around an electrode array in Example 2 following 12 weeks of implantation (scale bar=10 mm)

The electrode arrays were configured to flatten the nerve and increase surface area contact with corresponding electrode surfaces. Despite this, an absence of tissue adhesions was found, indicating that the electrode array could be removed from its installation site with minimal trauma to the underlying nerve, while performing adequately in situ. The ability to safely remove an electrode array is an important design consideration for the development of a safe device for clinical application. Taken together, these results indicate benefits of embodiments of the present disclosure, showing that chronic implantation of a peripheral nerve such as the vagus nerve using these embodiments is safe, functional and has highly translatable application. FIG. 13 is an in vivo macroscopic observation of the implanted array from an autopsy, which shows the typical gross tissue response around the electrode array in this example, following 12 weeks of implantation and illustrates the vagus nerve (VN) in addition to the electrode array and cable. In FIG. 13, the scale bar indicates 10 mm.

As described above, the electrode array in the present example included a first recording electrode pair (E3-E4) 10 mm from a stimulating electrode pair (E1-E2) and a second recording electrode pair (E5-E6) 20 mm from the stimulating electrode pair (E1-E2). A subpopulation of thoracic vagal fibres have short latencies, and a benefit was found in having a longer distance (e.g. 20 mm) between the stimulating electrode pair (E1-E2) and recording electrodes (E5-E6) in order to record electrical responses outside the latency of the stimulus artefact. In contrast, a majority of thoracic vagal fibres have slower conductions and are poorly synchronized. Recordings of these electrical responses were therefore diminished over longer distances (e.g. 20 mm) between the stimulating electrode pair (E1-E2) and recording electrodes (E5-E6). Therefore, a benefit was found in having a shorter distance (e.g. 10 mm) between the stimulating electrode pair (E1-E2) and recording electrodes (E3-E4) in order to record electrode responses for slow conduction fibre types.

The electrically-evoked slower conduction fibres had an average conduction of 1.4 m/s. This is in the same range as C-fibre conduction, suggesting that it is likely the slow conduction fibres evoked by the vagus nerve array and recorded at a site 10 mm from the site of stimulation are indeed C-fibres, and that stimulation levels were suprathreshold throughout the duration of the study. As it is believed that the anti-inflammatory mechanism of action for alleviating inflammatory diseases (e.g. IBD) is via the activation of C-fibres, the ability of the present embodiment to record evoked neural potentials that were likely to be C-fibres may be beneficial, e.g. for treating IBD or otherwise.

Figure 14:
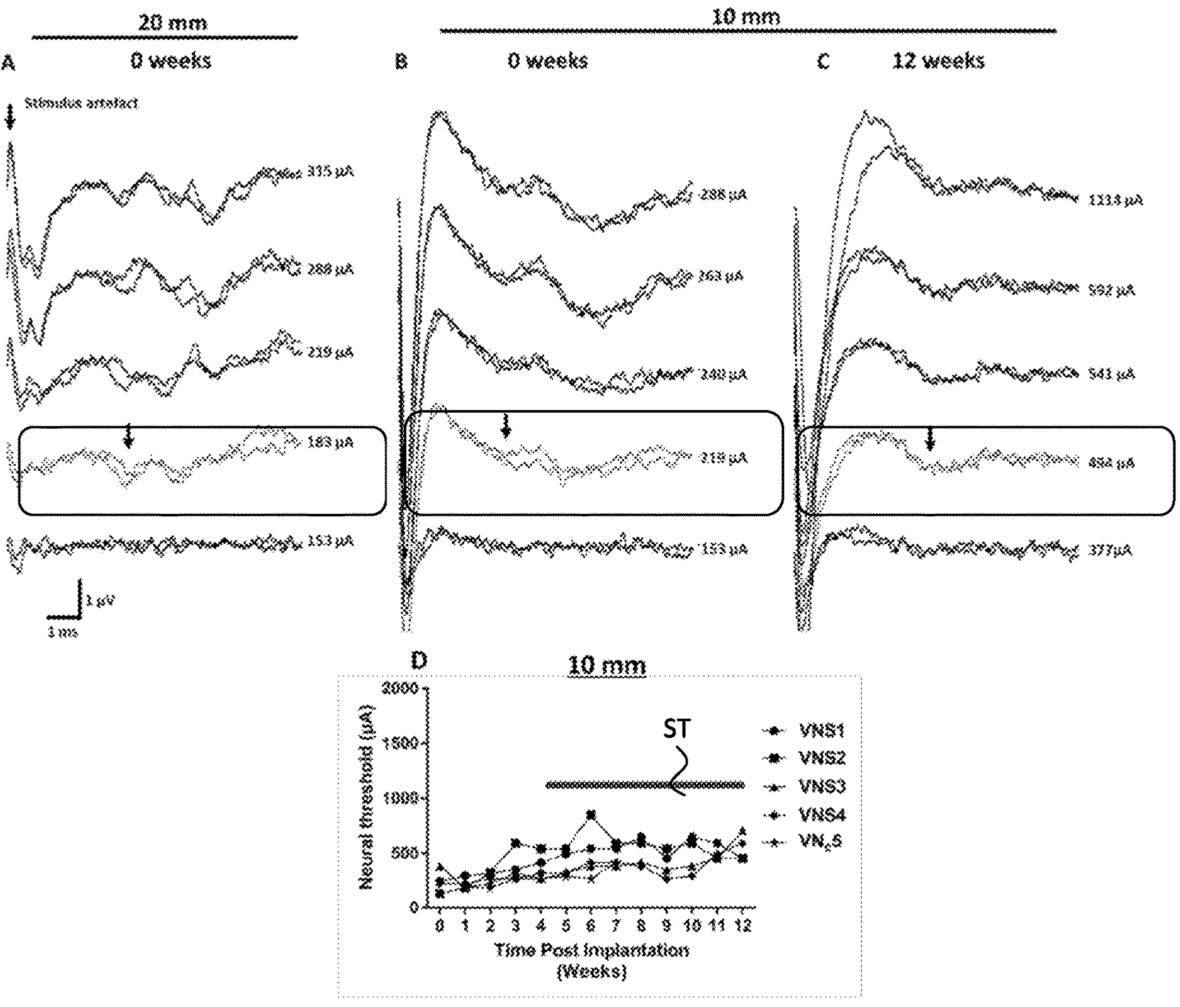
FIG. 14 shows electrophysiological recordings of a vagus nerve during an implantation period in Example 2.

FIG. 14 shows electrophysiological recordings of the vagus nerve during the implantation period. In A: ECAPs (indicated by arrow) of faster conduction fibres were detected using recording electrodes 20 mm from the stimulating electrodes pairs at 0 weeks (latency: 4.4 ms, conduction: 4.5 m/s). In B-C: ECAPs of slower conduction fibres were recorded at a site 10 mm from stimulating electrodes at 0 weeks (B, latency: 4.1 ms, conduction: 1.4 m/s) and 12 weeks (C, latency: 5.0 ms, conduction: 2 m/s) from the same animal (VNS4). In D: Quantification of neural response thresholds (indicated by the recordings in A-C highlighted by rectangular outlines) from 10 mm electrode configuration (T=0) show no changes (P=0.49) in thresholds over the implantation period. The bar ST indicates the stimulation period. In A-C, the arrows indicate the times of the ECAP peak at the recording electrode.

This example also may support the use of a peripheral nerve array according to one or more aspects of the present disclosure for VNS at a site located below the branches to the larynx, heart and lungs, as a treatment of inflammatory diseases.

An electrode array according to one or more aspects of the present disclosure may allow for the titration of stimulus parameters so that precise stimulation levels can be selected for optimal therapeutic benefit, while remaining safe, biocompatible and resulting in few sustained off-target effects. An electrode array according to one or more aspects of the present disclosure may alternatively or additionally aid in placing a device at suitable location such that occurrences of any off target effects can be reduced.

Example 3

Methods: An abdominal vagus nerve array was implanted in a male Sprague-Dawley rat under anaesthesia, and the animal was allowed to recover. At two weeks following implantation, evoked potentials were generated using a range of currents, to determine neural threshold, and the following stimulation parameters: 200 μs and 50 μs interphase gap; 10 Hz.

Results: There was a clear neural response at latency of 2.3 ms (indicated in FIG. 16C by arrow). The distance between electrodes 1-2 (stimulating pair) and electrodes 3-4 (recording pair) was 4 mm. Therefore the velocity of this response was 1.74 m/s, which falls within the range of C-fibre activity (0.5-2 m/s). This data showed that two weeks after implantation, our custom-made implanted abdominal vagus nerve array could successfully activate C-fibres, which are thought to be the key therapeutic fibres involved in driving anti-inflammatory mechanisms.

Example 4

Methods: At 2 weeks following vagus nerve implantation the ileus was inflamed with TNBS. Stimulation (10 Hz, 1.7 mA) was applied to awake rats (n=3) for 3 hours a day (30 seconds ON, 5 minutes OFF). Unstimulated rats were treated in the same way but did not receive stimulation. Following 5 days post TNBS injection, animals were sacrificed and inflamed tissue taken for histology. Tissue was stained for haematoxylin and eosin and eosinophils identified morphologically; T cells were identified using immunohistochemically using antibodies to CD3; neutrophils were identified using myeloperoxidase staining. Leukocyte populations were quantified within difference layers of the transmural wall.

Figure 18:
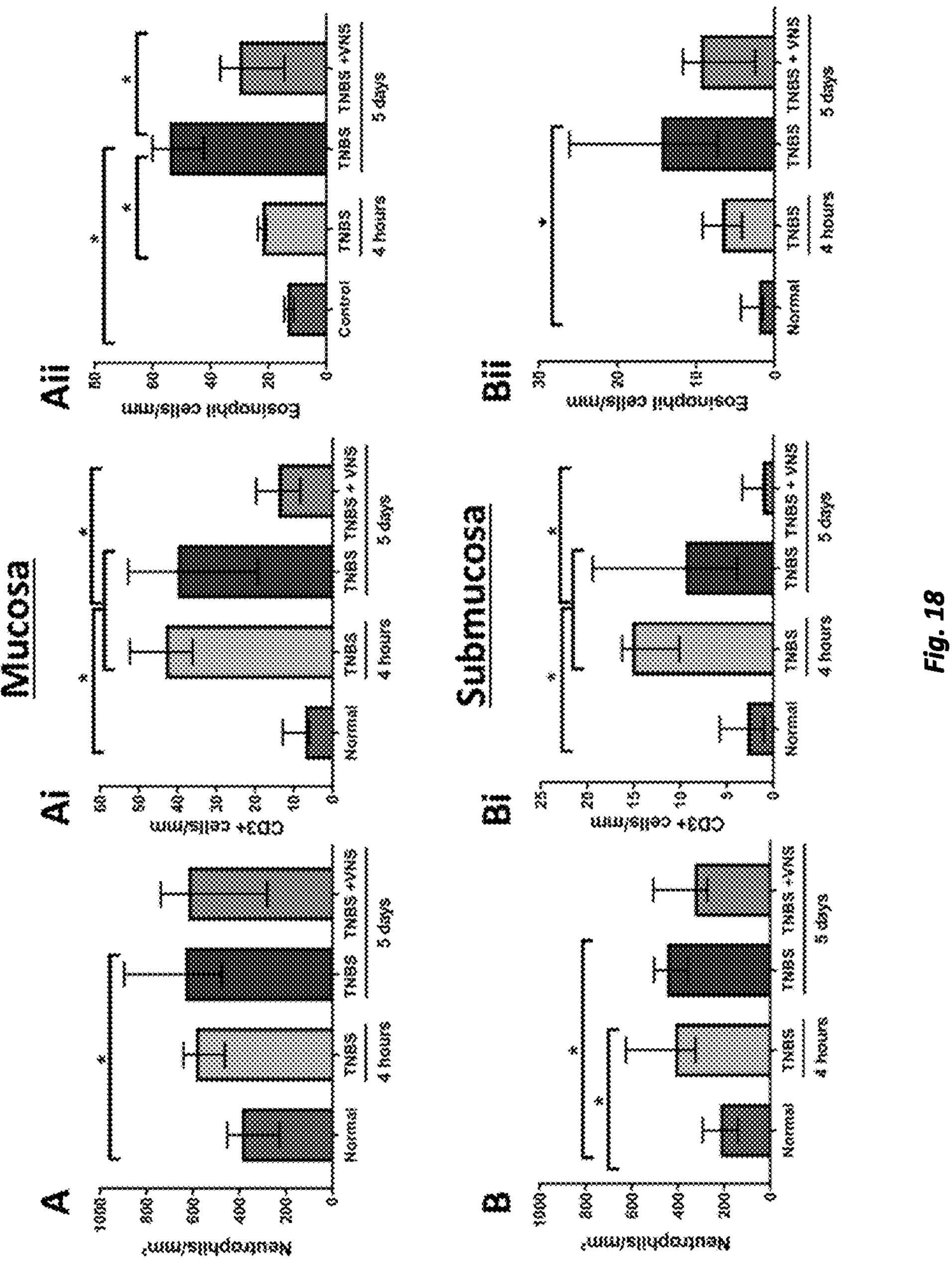
FIG. 18 shows that vagus nerve stimulation (VNS) reduces leukocyte infiltration into mucosa and submucosa layers following TNBS injection. A-Aii: At 5 days following TNBS injection, the prevalence of neutrophils, CD3+ cells and eosinophils increased within the mucosal layer ($P<0.05$). In VNS treated tissue, CD3+ cells and eosinophils were significantly reduced ($P<0.05$), while neutrophil cell counts were reduced to similar to that of normal ($P>0.05$). B-Bii: In the submucosa, TNBS injection induced an acute increase in neutrophils and CD3+ ($P<0.05$), while all leukocyte populations were elevated in unstimulated submucosa tissue at 5 days ($P<0.05$). However, in VNS tissue CD3+ cells were significantly reduced, while MPO+ cells and eosinophils were similar to that of normal ($P>0.05$). Data show median+interquartile range. Differences between groups ($P<0.05$) were tested using non-parametric Kruskal-Wallis and Dunn's post hoc test.

Results:

Mucosal tissue: At 5 days following TNBS injection, the prevalence of neutrophils, CD3+ cells and eosinophils increased within the mucosal layer (P<0.05) (FIGS. 18A-18Aii). In VNS treated tissue, CD3+ cells and eosinophils were significantly reduced (P<0.05) (FIGS. 18Ai-18Aii), while neutrophil cell counts trended towards a reduction in numbers. In the submucosa, TNBS injection induced an acute increase in neutrophils and CD3+ (P<0.05), while all leukocyte populations were elevated in unstimulated submucosa tissue at 5 days (P<0.05) (FIGS. 18B-18Bii). However, in VNS-treated tissue, CD3+ cells were significantly reduced, while neutrophils cells and eosinophils trended towards a reduction in numbers.

External muscle layers: At 5 days following TNBS injection, the prevalence of neutrophils, and eosinophils increased within circular and longitudinal muscle layers (P<0.05) (FIG. 19A-19Aii). In VNS treated tissue, neutrophils, CD3+ cells and eosinophils were significantly reduced (P<0.05). Data show median+standard error. Differences between groups (P<0.05) were tested using non-parametric Kruskal-Wallis and Dunn's post hoc test.

Example 5

Methods: At 2 weeks following the implantation of the vagus nerve array, rats received an injection of TNBS (day 1). At days 2, 3 and 5 post TNBS injection peripheral bloods form tail veins were taken for analysis of C-reactive protein content using an ELISA kit, a clinically used marker of inflammation.

As shown in FIG. 20, TNBS injection induced a transient increase in CRP levels at 2 days (P<0.05), which significantly decreased to normal levels by day 5 (P<0.05). Following VNS treatment, levels of CRP in plasma were significantly less in unstimulated at 2 days (P<0.05). Data (n=3/group) were normalised to control values and show mean proportional changes (%)+S.E, and significant differences accepted as P<0.05.

Example 6

The systemic effects of ileitis were assessed in rats by evaluating the stool consistency and indicators of stress (adapted from Sun et al., 2013, PLOS ONE, 8(8):e69424), as set out in Table 2.

Scoring of the Disease activity index (DAI) shown in Table 2. Measurements generated on Day 1, prior to TNBS injection, were used as the control. The total stool score over the 4 days (total out of 8, i.e. max total of 2/day) following TNBS injection were combined and converted into a percentage. Similarly, the total stress score over the 4 days (total out of 8, i.e. max total of 2/day) following TNBS injection were combined and converted into a percentage.

TABLE 2

| | Severity of changes in animal's disease activity index | | | |
|---|---|---|---|---|
| Variable | 0 | 1 | 2 | Score |
| Stool analysis | Normal: hard pellet shaped form | Loose: Pellet is sticky and deforms under pressure | Diarrhoea: No form; faecal matter adherent to fur. | 0-2/2 |

TABLE 2-continued

| | Severity of changes in animal's disease activity index | | | |
|---|---|---|---|---|
| Variable | 0 | 1 | 2 | Score |
| Signs of stress | No stress 1. No fur discoloration; 2. Eye lids clear of discharge | Mild Stress 1. Pink discolouration at base on neck 2. Eye lids clear of discharge | High stress 1. Pink discolouration at base on neck 2. Eye lids have red discharge | 0-2/2 |

The behavioural effects of ileitis were assessed in rats by evaluating weight, stool quality and indicators of stress (adapted from Sun et al., 2013). Rats were weighed for 5 consecutive days prior to surgery (during the habituation period) and during the 5 days post TNBS injection at exactly the same time each day (9:30 am). Normal stool had a hard, pellet-shaped form; loose stools were 'sticky' or slightly wet, and deformed under pressure; diarrhoea had no form and faecal matter was adherent to fur. Stool generated over night by rats was assessed at the same time each morning. Rats were placed into clean cages following the morning stool assessment. Animals were also monitored for signs of stress. Normal unstressed rats had no pink discolouration around the nape of the neck or eyes; mild stress was indicated when rats had pink discolouration on the nape of the neck; high stress was indicated when rats had pink discolouration around the neck and the eyes/eye lids were associated with a red discharge. Stool consistency and signs of stress were assessed daily at the same time each morning. Measurements generated on day 1, prior to TNBS injection, were used as the control. The total stool and stress score for the 4 days (total out of 8) following TNBS injection were combined and converted into a percentage.

Vagus Nerve Stimulation Reduced the Severity of Ileitis Symptoms

Control rats produced stools that were solid pellets and had no signs of stress (parameters described in Table 2). Following TNBS injection, loose stools or diarrhoea were observed every day in unstimulated rats and significantly worse than control (P<0.05). However, the stool quality of stimulated rats was similar to that of control (P>0.05; FIG. 21A), with only one animal transiently producing loose stool. Symptoms of stress were also significantly higher in unstimulated rats, compared to control (P<0.05). However, signs of stress were less prevalent in stimulated animals, which was similar to that of control rats (P>0.05; FIG. 21B).

Example 7

Vagus Nerve Array Implantation Surgery

All surgical procedures were performed under aseptic conditions. Abdominal vagus nerve implantation: Rats were anaesthetised and the skin incised on the ventral abdominal midline and along the dorsal-lumbar aspect of the spine. The vagus nerve array was tunnelled subcutaneously from the dorsal-lumbar incision to exit through the ventral abdominal incision. The abdominal cavity was exposed and the liver retracted gently using sterile saline soaked gauze. Abdominal tissue was kept moist at all times using warm sterile saline. The sub-diaphragmatic anterior abdominal branch of the vagus nerve was identified (FIG. 15). The segment of vagus nerve rostral to the hepatic-celiac junction was detached from the underlying oesophagus and the array inserted at this location. The array was sutured (7-0 silk, Ethicon) to the oesophagus to provide stabilisation. The abdominal cavity and skin was sutured closed in two layers. The rat was rotated to expose the dorsal aspect of the spine. The percutaneous pedestal was anchored to the connective tissue of the lumbar region of the spine and the skin closed around the percutaneous pedestal. Therapeutic electrical stimulation was delivered via this percutaneous connector.

Measuring Off-Target Effects to Stimulation

In a series of acute experiments (n=5) changes to heart rate, breathing and blood pressure were measured during cervical or abdominal vagus nerve stimulation. The cervical vagus nerve was exposed and identified for implantation. A vagus nerve array (FIG. 16A, B) was then implanted onto the nerve. In the same rat, the abdominal vagus nerve was also implanted (see section above). To measure arterial blood pressure changes, the femoral artery was cannulated and connected to a transducer. Respiration patterns (i.e. breathing rate and amplitude) were recorded in isoflurane anaesthetised, freely breathing rats by placing a piezo-electric respiration band around the thorax. Care was taken to place the respiratory band sensor over the point of largest excursion during respiration. Heart rate was measured by recording ECG signals by placing needles (26 Gauge) across the thorax and a return in the left legs. The ECG signal was amplified using a WPI Iso-80 bioamp (Gain: ×1000; high pass: 5 Hz; low pass 10 kHz). Baseline recordings were generated for 30 seconds (no stimulation applied), followed by 20 seconds of stimulation (10 Hz, 50 repetitions) of the cervical or abdominal vagus nerve at current levels individually tested between 0-2 mA (100 μA steps; 200 μs pulse width). Following stimulation, a further 30 seconds of recordings were taken to allow the system to return to normal. Heart rate, breathing rate, breathing amplitude and blood pressure changes from baseline were calculated from the waveforms using a detection algorithm in the IGOR8 software.

Figure 22:
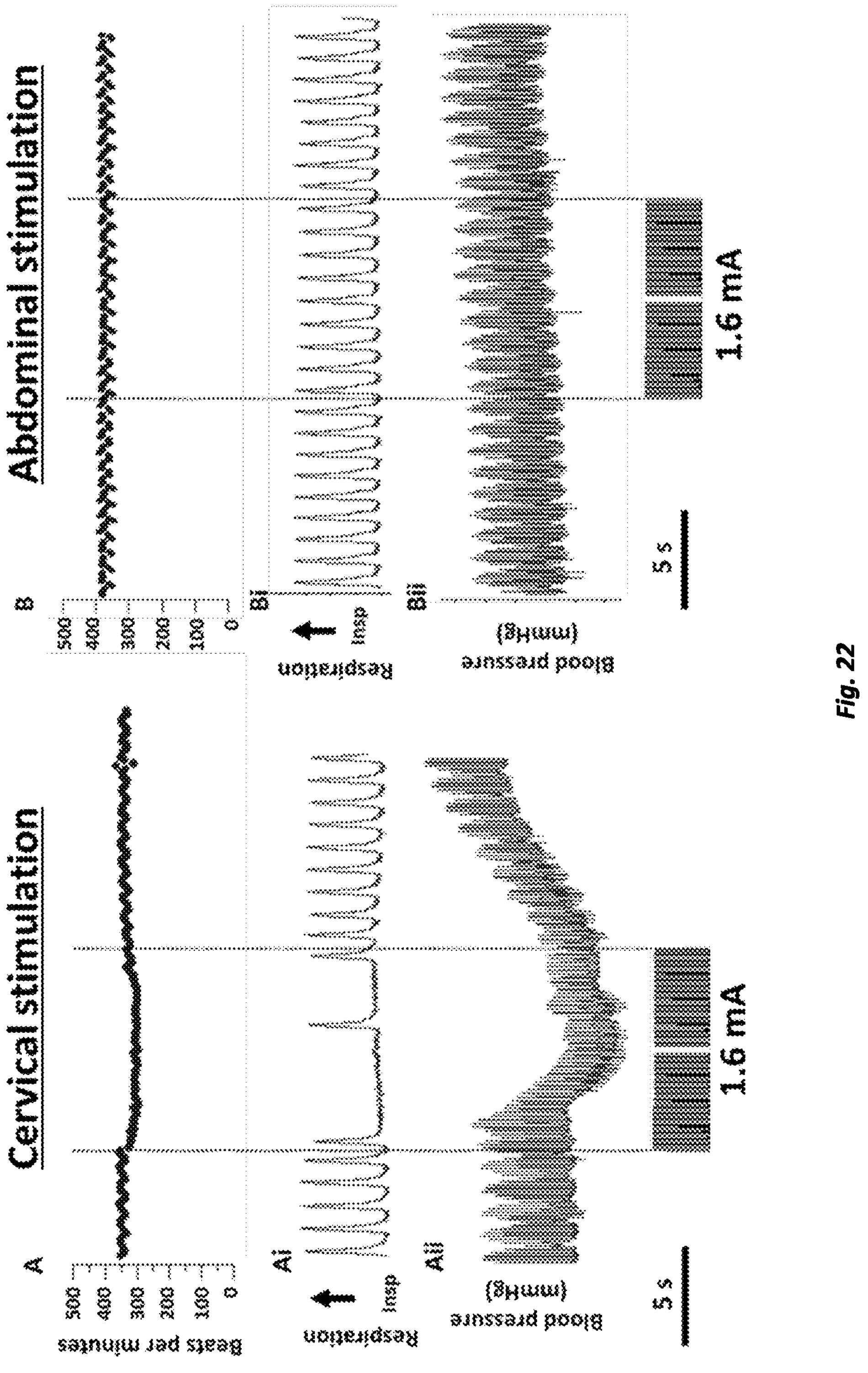
FIG. 22 shows that no off target effects are seen when the abdominal vagus nerve is stimulated at surpathreshold levels. A-Aii: A decrease in heart rate (A), respiratory rate (Ai) and blood pressure (Aii) occurred during 1.6 mA cervical vagus nerve (D). B-Bii: No changes in heart rate (B), respiratory rate (Bi) and blood pressure (Bii) were seen during abdominal vagus nerve was stimulation (10 Hz, 1.6 mA).
Figure 23:
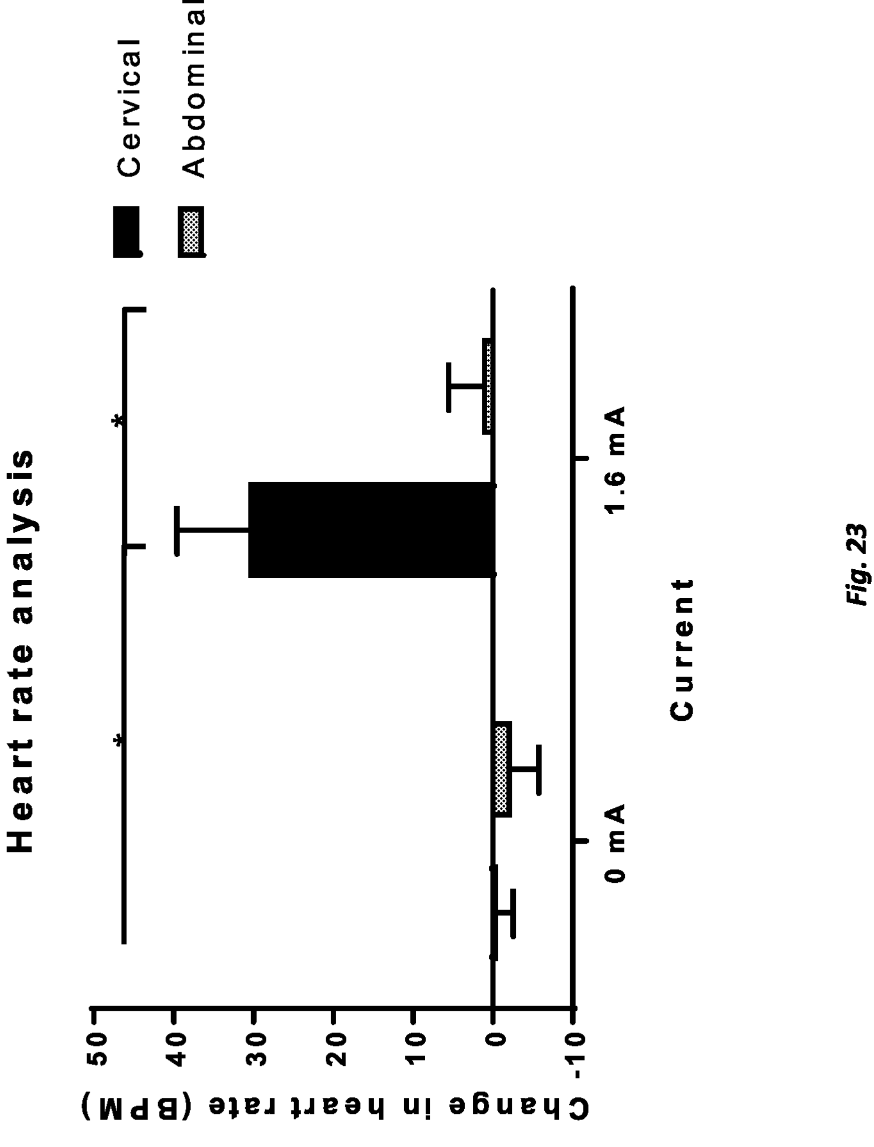
FIG. 23 shows bar graphs illustrating change in heart rate (beats per minute) when cervical versus abdominal stimulation locations are used. Differences in the change in heart rate (beats per minute) between stimulation location (cervical×abdominal) and current level (0 mA, superthreshold, ×1.6 mA, suprathreshold) were tested using an RM two-way ANOVA (n=5; Current: P=0.056; Location: P=0.0424; Interaction: P=0.0192). During cervical stimulation at current level 1.6 mA, heart rate decreased by 31±9 beats/minute (P=0.013), compared to 0 mA (4±2). However, during abdominal stimulation at 1.6 mA, heart rate remained similar to 0 mA (P=0.883). Furthermore, heart rate was significantly reduced during 1.6 mA cervical stimulation when compared to 1.6 mA abdominal stimulation delivered at 1.6 mA (P=0.0159).

Results: No Measurable Off Target Affects During Abdominal Vagus Nerve Stimulation Differences in the change in heart rate (beats per minute) were tested between stimulation location (cervical×abdominal) and current level (0 mA, superthreshold, ×1.6 mA, suprathreshold) were tested using an RM two-way ANOVA (n=5; Current: P=0.056; Location: P=0.0424; Interaction: P=0.0192). During cervical stimulation at current level 1.6 mA, heart rate decreased by 31±9 beats/minute (P=0.013; FIG. 22A), compared to 0 mA (4±2). However, during abdominal stimulation at 1.6 mA, heart rate remained similar to 0 mA (P=0.883). Furthermore, heart rate was significantly reduced during 1.6 mA cervical (FIGS. 22A and 23) stimulation when compared to 1.6 mA abdominal stimulation delivered at 1.6 mA (P=0.0159; FIGS. 22B and 23). Respiration recordings were noisy and could not be reliably quantified. This is perhaps due to the amount of pressure required to close the respiratory band around the rat's chest cavity, which resulted in the recording of inconsistent breathing patterns over time (within the same animal). However, visual observations of rat's (n=5) respiration confirmed that there were changes to the pattern during 1.6 mA cervical stimulation (FIG. 22Ai). However, no obvious changes in breathing (n=5) were observed during 1.6 mA abdominal stimulation (FIG. 22Bi). Furthermore, as blood pressure changes were only assessed in n=2 animals, data were not quantified. However, from our visual inspection of blood pressure recordings (n=2), we observed an abrupt decrease that coincided with the start of the 1.6 mA cervical stimulus period (FIG. 22Aii), while no changes to blood pressure were observed during 1.6 mA abdominal stimulation (FIG. 22Bii).

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive. For instance, it will be appreciated that differences in physiologies amongst humans, or between humans and other animals may lead to variations and/or modifications from above-described embodiments, without departing from scope of the present disclosure.

The invention claimed is:

1. A method for treating rheumatoid arthritis in a human subject in need thereof, comprising:

implanting or having implanted in the human subject two or more electrodes provided in an electrode array at a site below the cardiac branches and above the hepatic-celiac branches of the vagus nerve, wherein the two electrodes in the electrode array are located just below the diaphragm of the human subject;

through the two or more implanted electrodes in the provided electrode array, providing to the human subject a therapeutically effective electrical stimulation of the anterior central abdominal vagus nerve or the posterior central abdominal vagus nerve, wherein: the stimulation comprises delivering biphasic pulses comprising a pulse width of about 250 μsec, a stimulation frequency of about 10 Hertz; and a current of about 2 mA; and detecting one or more evoked responses in the central abdominal vagus nerve following the electrical stimulation;

and whereby the rheumatoid arthritis is treated in the human subject.

2. The method according to claim 1, wherein:

(i) the anterior central abdominal vagus nerve is stimulated;

(ii) the posterior central abdominal vagus nerve is stimulated; or (iii) both the anterior abdominal vagus nerve and posterior central abdominal vagus nerve are stimulated.

3. The method according to claim 1, wherein the therapeutically effective electrical stimulation is provided multiple times.

4. The method according to claim 3, wherein stimulation settings are adjusted based on properties of detected evoked responses.

5. The method according to claim 1, further comprising administering to the subject a therapeutically effective amount of a therapeutic agent for treating a chronic inflammatory condition.

6. The method according to claim 5, wherein the therapeutic agent is an anti-inflammatory drug, an immunosuppressant, or an antibiotic.

* * * * *